United States Patent [19]

Maier et al.

[11] Patent Number: 5,455,273
[45] Date of Patent: Oct. 3, 1995

[54] N,N-DISUBSTITUTED ARYLCYCLOALKYLAMINES, THE SALTS THEREOF, PHARMACEUTICAL COMPOSITIONS CONTAINING THESE COMPOUNDS AND THE USE THEREOF AND PROCESSES FOR PREPARING THEM

[75] Inventors: Roland Maier, Biberach; Peter Müller, Mittelbiberach; Eberhard Woitun, Biberach; Rudolf Hurnaus, Biberach; Michael Mark, Biberach; Bernhard Eisele, Biberach; Ralph-Michael Budzinski, Biberach; Gerhard Hallermayer, Maselheim-Sulmingen, all of Germany

[73] Assignee: Karl Thomae GmbH, Biberach an der Riss, Germany

[21] Appl. No.: 154,644

[22] Filed: Nov. 19, 1993

[30] Foreign Application Priority Data

Nov. 20, 1992 [DE] Germany .................. 42 39 151.2

[51] Int. Cl.[6] .................................................. A61K 31/165
[52] U.S. Cl. .................. 514/617; 514/438; 514/448; 514/510; 514/521; 514/523; 514/530; 514/531; 514/529; 514/535; 514/538; 514/539; 514/534; 514/542; 514/546; 514/549; 514/601; 514/602; 514/604; 514/605; 514/616; 514/613; 514/624; 514/627; 514/629

[58] Field of Search ................... 514/438, 448, 514/510, 512, 521, 530, 531, 535, 529, 549, 546, 602, 604, 601, 617, 624, 613, 627, 629, 605, 616, 523, 534, 538, 539, 542

[56] References Cited

U.S. PATENT DOCUMENTS 3,979,444  9/1976  Ledniler .

Primary Examiner—Michael L. Shippen
Attorney, Agent, or Firm—R. P. Raymond; M.E. M. Devlin; A. R. Stempel

[57] ABSTRACT

The invention relates to N,N-disubstituted arylcycloalkylamines of general formula

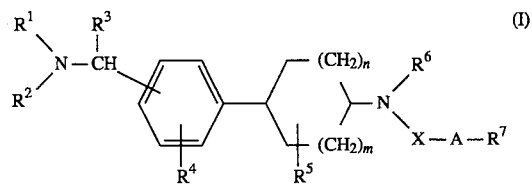

wherein n, m, A, X and $R^1$ to $R^7$ are defined as in claim 1, the isomers, isomer mixtures and salts thereof, which have valuable properties, particularly an inhibitory effect on cholesterol biosynthesis.

2 Claims, No Drawings

N,N-DISUBSTITUTED ARYLCYCLOALKYLAMINES, THE SALTS THEREOF, PHARMACEUTICAL COMPOSITIONS CONTAINING THESE COMPOUNDS AND THE USE THEREOF AND PROCESSES FOR PREPARING THEM

The present invention relates to N,N-disubstituted arylcycloalkylamines, the salts thereof with physiologically acceptable organic and inorganic acids, processes for preparing these compounds and pharmaceutical compositions containing them and the use thereof.

The compounds according to the invention are inhibitors of cholesterol biosynthesis, in particular inhibitors of the enzyme 2,3-epoxysqualene-lanosterol cyclase, a key enzyme of cholesterol biosynthesis. The compounds according to the invention are suitable for the treatment and prophylaxis of hyperlipidaemias, hypercholesterolaemias and of atherosclerosis. Further possible applications include the treatment of hyperproliferative skin and vascular disorders, tumours, gallstone trouble and mycoses.

Compounds which intervene in cholesterol biosynthesis are important for the treatment of a number of syndromes. Particular mention may be made in this regard of hypercholesterolaemias and hyperlipidaemias, which are risk factors for the occurrence of atherosclerotic vascular changes and their sequelae such as, for example, coronary heart disease, cerebral ischaemia, intermittent claudication and gangrene.

The importance of excessive serum cholesterol levels as a main risk factor for the occurrence of atherosclerotic vascular changes is generally recognized. Extensive clinical studies have led to the realization that the risk of suffering from coronary heart diseases can be decreased by reduction of the serum cholesterol (Current Opinion in Lipidology 2(4): 234 [1991]). Since the majority of the cholesterol in the body is self-synthesized and only a small part is absorbed from food, the inhibition of biosynthesis represents a particularly attractive method of lowering increased cholesterol levels.

In addition, treatment of hyperproliferative skin and vascular disorders and of oncoses, the treatment and prophylaxis of gallstone trouble and use in mycoses are described as further possible applications for cholesterol biosynthesis inhibitors. In this connection, in the latter case, intervention in ergosterol biosynthesis in fungal organisms, proceeds to a large extent in a manner analogous to the intervention in cholesterol biosynthesis in mammalian cells.

Cholesterol or ergosterol biosynthesis proceeds, starting from acetic acid, via a relatively large number of reaction steps. This multistage process offers a number of possibilities for intervention, of which the following may be mentioned as examples:

β-Lactones and β-lactams having potential anti-hypercholesterolaemic action which inhibit the enzyme 3-hydroxy-3-methylglutaryl-coenzyme A (HMG-CoA) synthase have been described (see J. Antibiotics 40, 1356 [1987], U.S. Pat. No. 4,751,237, EP-A-0462667 and U.S. Pat. No. 4,983,597).

Inhibitors of the enzyme HMG-CoA reductase are 3,5-dihydroxycarboxylic acids of the statin type and their δ-lactones, whose representatives lovastatin, simvastatin and pravastatin are used in the therapy of hypercholesterolaemias. Further possible applications of these compounds are in the treatment of fungal infections (U.S. Pat. No. 4,375,475, EP-A-0113881, U.S. Pat. No. 5,106,992), skin disorders (EP-A-0,369,263) and gallstone trouble and oncoses (U.S. Pat. No. 5,106,992; Lancet 339, 1154–1156 [1992]). Another possible therapy is the inhibition of smooth muscle cell proliferation by lovastatin (Cardiovasc. Drugs Ther. 5, Suppl. 3, 354 [1991]).

Inhibitors of the enzyme squalene synthetase, e.g. isoprenoid-(phosphinylmethyl)-phosphonates, and their suitability for the treatment of hypercholesterolaemias, gallstone trouble and oncoses is described in EP-A-0409181 and J. Med. Chemistry 34, 1912 [1991], and moreover cholesterol-lowering and antimycotic squalestatins are described in J. Antibiotics 45, 639–647 [1992] and J. Biol. Chemistry 267, 11705–11708 [1992].

Allylamines, such as naftifine and terbinafine which have found their way into therapy as agents against fungal disorders, are known as inhibitors of the enzyme squalene epoxidase as are allylamine NB-598 which has antihypocholesterolaemic action (J. Biol. Chemistry 265, 18075–18078, [1990]) and fluorosqualene derivatives which have hypercholesterolaemic action (U.S. Pat. No. 5,011,859). In addition, piperidines and azadecalins with potential hypocholesterolaemic and/or antifungal activity, whose mechanism of action is not unequivocally clarified and which are squalene epoxidase and/or 2,3-epoxysqualenelanosterol cyclase inhibitors, have been described (EP-A-0420116, EP-A-0468434, U.S. Pat. No. 5084461 and EP-A-0468457).

Examples of inhibitors of the enzyme 2,3-epoxysqualene-lanosterol cyclase are diphenyl derivatives (EP-A-0464465), aminoalkoxybenzene derivatives (EP-A-0410359) and piperidine derivatives (J. Org. Chem. 57, 2794–2803 [1992]), which have antifungal activity. In addition, this enzyme is inhibited in mammalian cells by decalins, azadecalins and indane derivatives (WO 89/08450, J. Biol. Chemistry 254, 11258–11263 [1981], Biochem. Pharmacology 37, 1955–1964 [1988] and JP 64/003144), and also by 2-aza-2,3-dihydrosqualene and 2,3-epiminosqualene (Biochem. Pharmacology 34, 2765–2777 [1985]), by squalenoid epoxide vinyl ethers (J. Chem. Soc. Perkin Trans. I, 461 (1988)) and 29-methylidene- 2,3-oxidosqualene (J. Amer. Chem. Soc. 113, 9673–9674 [1991]).

Finally, as inhibitors of the enzyme lanosterol-14α-demethylase one may also mention steroid derivatives with potential antihyperlipaemic action and which simultaneously affect the enzyme HMG-CoA reductase (U.S. Pat. No. 5,041,432, J.Biol Chemistry 266, 20070–20078 [1991], U.S. Pat. No. 5,034,548). In addition, this enzyme is inhibited by the antimycotics of the azole type as represented by N-substituted imidazoles and triazoles. This class includes, for example, the commercially available antimycotics ketoconazole and fluconazole.

The compounds of the following general formula I are novel. Surprisingly it has been found that they are very effective inhibitors of the enzyme 2,3-epoxysqualene-lanosterol cyclase (International Classification: EC5.4.99.7).

The enzyme 2,3-epoxysqualene-lanosterol cyclase catalyzes a key step in cholesterol or ergosterol biosynthesis, namely the conversion of 2,3-epoxysqualene to lanosterol, the first compound with steroid structure in the biosynthetic cascade. Compared to inhibitors of earlier biosynthetic steps, such as, for example, HMG-CoA synthase and HMG-CoA reductase, the advantage of greater selectivity can be expected from inhibitors of this enzyme, since the inhibition of the earlier biosynthetic steps leads to the decrease of biosynthetically formed mevalonic acid and as a result can also adversely affect the biosynthesis of the mevalonic acid-dependent substances dolichol, ubiquinone and isopentenyl-t-RNA (cf. J. Biol. Chemistry 265, 18075–18078 [1990]).

In the case of inhibition of biosynthetic steps after the conversion of 2,3-epoxysqualene to lanosterol, there is the risk of the accumulation of intermediate products with steroid structure in the body and the triggering of the resultant toxic effects. This is described, for example, for triparanol, a desmosterol reductase inhibitor. This substance had to be withdrawn from the market because of the formation of cataracts, ichthyosis and alopecia (cited in J. Biol. Chemistry 265, 18075- 18078 [1990]).

As already stated at the beginning, inhibitors of 2,3-epoxysqualene-lanosterol cyclase are occasionally described in the literature. The structures of these compounds, however, are completely different from the structure of the compounds according to the invention of the below-mentioned general formula I.

The invention relates to the provision of antihypercholesterolaemic substances which are suitable for the treatment and prophylaxis of atherosclerosis and which, in contrast to known active compounds, are distinguished by a better antihypercholesterolaemic action and have greater selectivity and thus greater safety. Since the compounds according to the invention can also inhibit ergosterol biosynthesis in fungal organisms on account of their high activity as inhibitors of the enzyme 2,3-epoxysqualene-lanosterol cyclase, they are also suitable for the treatment of mycoses.

The N,N-disubstituted arylcycloalkylamines of the present invention and the salts thereof have the general formula I. The compounds can optionally also be present in the form of enantiomers, diastereomers or mixtures thereof.

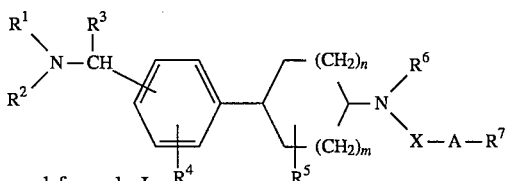

In general formula I, n represents the number 1 or 2, m represents the number 0 or 1, A denotes a single bond, a straight-chained or branched $C_{1-17}$-alkylene group, a $C_{2-17}$-alkenylene group or a $C_{2-4}$-alkynylene group, X is a carbonyl or sulphonyl group, $R^1$ is a straight-chained or branched $C_{1-5}$-alkyl group, $R^2$ is a straight-chained or branched $C_{1-5}$-alkyl group which may be substituted by one or two hydroxy groups, by an alkoxy or by an alkylcarbonyloxy group having 1 to 5 carbon atoms in the alkyl moiety, the alkyl moiety being straight-chained or branched, by an alkoxycarbonyloxy group, whilst the above-mentioned substituents may not be bound in position 1 of the alkyl group and two of these groups may not be bound to the same carbon atom, or by an aminocarbonyl, alkylaminocarbonyl, dialkylaminocarbonyl, cyano or alkylcarbonyl group, $R^3$, $R^4$ and $R^5$ which may be identical or different, each denote a hydrogen atom or an alkyl group, $R^6$ denotes a hydrogen atom, a straight-chained or branched $C_{1-6}$-alkyl group, a $C_{3-6}$-cycloalkyl group, an allyl or propargyl group or an optionally halogen-substituted benzyl group, $R^7$ denotes a hydrogen atom, a $C_{3-6}$-cycloalkyl group, a phenyl group optionally substituted by an alkyl group, by one or two halogen atoms or by a trifluoromethyl group, or $R^7$ denotes a naphthyl or tetrahydronaphthyl group or a thienyl group optionally substituted by a halogen atom or by an alkyl group, whilst A cannot be a single bond if X is a sulphonyl group and $R^7$ is a hydrogen atom, and unless otherwise specified the above-mentioned alkyl and alkoxy moieties may each contain 1 to 3 carbon atoms and the above-mentioned halogen atoms may each denote a fluorine, chlorine or bromine atom.

Preferred compounds of general formula I are those wherein:

n is the number 1; m is the number 1;

A is a single bond, a straight-chained or branched $C_{1-17}$-alkylene group or a $C_{2-4}$-alkenylene group;

X is a carbonyl or sulphonyl group;

$R^1$ is a straight-chained or branched $C_{1-5}$-alkyl group;

$R^2$ is a straight-chained or branched $C_{1-5}$-alkyl group which may be substituted by one or two hydroxy groups, by an alkoxy or by an alkylcarbonyloxy group having 1 to 5 carbon atoms in the alkyl moiety, whilst the alkyl moiety may be straight-chained or branched, or by an alkoxycarbonyloxy group, whilst the above-mentioned substituents may not be bound in position 1 of the alkyl group and two of these groups may not be bound to the same carbon atom, or by an aminocarbonyl, cyano or alkylcarbonyl group;

$R^3$ denotes a hydrogen atom or an alkyl group;

$R^4$ and $R^5$, which may be identical or different, each denote a hydrogen atom or a methyl group;

$R^6$ denotes a straight-chained or branched $C_{1-6}$-alkyl group, a $C_{3-6}$-cycloalkyl group, an allyl or propargyl group or an optionally halogen-substituted benzyl group;

$R^7$ denotes a hydrogen atom, a $C_{3-6}$-cycloalkyl group or a phenyl group optionally substituted by 1 or 2 halogen atoms or by a trifluoromethyl group;

whilst A cannot be a single bond if X is a sulphonyl group and $R^7$ is a hydrogen atom, and unless otherwise specified the above-mentioned alkyl and alkoxy moieties may each contain 1 to 3 carbon atoms and the above-mentioned halogen atoms may each represent a fluorine, chlorine or bromine atom, and the enantiomers, diastereomers and salts thereof.

Particularly preferred compounds of general formula I are those wherein:

n is the number 1; m is the number 1;

A is a single bond, a straight-chained or branched $C_{1-17}$-alkylene group or a 2-propenylene group;

X is a carbonyl or sulphonyl group;

$R^1$ is a straight-chained or branched $C_{1-5}$-alkyl group;

$R^2$ is a straight-chained or branched $C_{1-5}$-alkyl group which may be substituted by one or two hydroxy groups, by an alkoxy or by an alkylcarbonyloxy group having 1 to 4 carbon atoms in the alkyl moiety, whilst the alkyl moiety may be straight-chained or branched, or by an alkoxycarbonyloxy group, whilst the above-mentioned substituents may not be bound in position 1 of the alkyl group and two of these groups may not be bound to the same carbon atom, or by an aminocarbonyl, cyano or alkylcarbonyl group;

$R^3$ denotes a hydrogen atom or a methyl group;

$R^4$ and $R^5$ each denote a hydrogen atom;

$R^6$ denotes a straight-chained or branched $C_{1-3}$-alkyl group, a cyclopropyl group, an allyl or propargyl group or an optionally fluorine-substituted benzyl group;

$R^7$ denotes a hydrogen atom, a cyclohexyl group, a phenyl group optionally substituted in the 4-position by a chlorine atom or by a trifluoromethyl group, or $R^7$ denotes a 3,4-dichlorophenyl group, a 4-chloro-3-methylphenyl group, a 5-methyl-2-thienyl group, a 5-chloro- 2-thienyl group or a 1,2,3,4-tetrahydronaphthyl group;

whilst A cannot be a single bond if X denotes a sulphonyl group and $R^7$ is a hydrogen atom, and unless otherwise specified the above-mentioned alkyl and alkoxy moieties may each contain 1 to 3 carbon atoms, and the enantiomers, diastereomers and salts thereof, but especially the compounds (1) trans-N-(4-chlorobenzenesulphonyl)-N-methyl-4-[4-(2-methoxyethyl)methylaminomethylphenyl]-cyclohexylamine (2) trans-4-(4-aminocarbonylmethyl-methylaminomethyl-phenyl)-N-( 4-chlorobenzenesulphonyl)-N-methylcyclohexylamine (3) trans-4-(4-aminocarbonylmethyl-methylaminomethyl-phenyl)-N-( 4-chlorobenzoyl)-N-methylcyclohexylamine (4) trans-N-(4-chlorobenzoyl)-N-methyl-4-[4-( 3-hydroxypropyl)methylaminomethylphenyl]-cyclohexylamine (5) trans-4-[4-(3-acetoxypropyl)methylaminomethylphenyl]-N-( 4-chlorobenzoyl)-N-methylcyclohexylamine (6) trans-N-(4-chlorobenzoyl)-N-methyl-4-[4-( 3-cyanopropyl)-methylaminomethylphenyl]-cyclohexylamine (7) trans-4-[4-( 1-aminocarbonylethyl)methylaminomethyl-phenyl]-N-( 4-chlorobenzoyl)-N-methylcyclohexylamine (8) trans-N-(4-chlorobenzoyl)-N-methyl-4-[4-(R- 2,3-dihydroxy-2-methylpropyl)methylaminomethylphenyl]-cyclohexylamine (9) trans-N-(4-chlorobenzoyl)-N-methyl-4-[4-( 2-hydroxy-ethyl)isopropylaminomethylphenyl]cyclohexylamine

(10) cis-N-(4-chlorobenzoyl)-N-methyl-4-[4-( 3-hydroxypropyl)methylaminomethylphenyl]-cyclohexylamine

(11) trans-4-[4-( 3-hydroxypropyl)methylaminomethylphenyl]-N-methyl-N-( 4-trifluoromethylbenzoyl)-cyclohexylamine

(12) trans-N-cyclohexylcarbonyl-N-methyl-4-[4-( 3-hydroxypropyl)methylaminomethylphenyl]-cyclohexylamine

(13) trans-N-(4-chloro-3-methylbenzoyl)-N-methyl-4-[4-(3-hydroxypropyl)methylaminomethylphenyl]-cyclohexylamine

(14) trans-N-(3,4-dichlorophenylacetyl)-N-methyl-4-[4-(3-hydroxypropyl)methylaminomethylphenyl]-cyclohexylamine

(15) trans-4-[4-( 3-hydroxypropyl)methylaminomethylphenyl]-N-methyl-N-( 1,2,3,4-tetrahydronaphthalene-2-carbonyl)-cyclohexylamine

(16) trans-N-(5-chlorothienyl-2-carbonyl)-N-methyl-4-[4-(3-hydroxypropyl)methylaminomethylphenyl]-cyclohexylamine the enantiomers, diastereomers and salts thereof.

Methods of Preparation

The compounds of general formula I can be prepared by the following methods:

a) By reacting compounds of general formula II

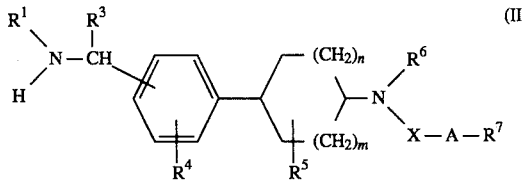

(wherein n, m, A, X, $R^1$ and $R^3$ to $R^7$ are as hereinbefore defined)

with a compound of general formula III $$R^2-Y \qquad\qquad (III)$$

wherein $R^2$ is as hereinbefore defined and Y denotes a reactive leaving group such as a halogen atom, e.g. a chlorine, bromine or iodine atom, or a sulphonyloxy group.

The reaction is conveniently carried out in a suitable solvent such as ethanol, tert.butanol, tetrahydrofuran, dimethylformamide or dimethylsulphoxide or in a mixture of the above-mentioned solvents, optionally in the presence of a base such as potassium carbonate, sodium carbonate or a tert.amine which is difficult to alkylate, such as N-ethyldiisopropylamine, at temperatures between 0° C. and 100° C., but preferably at a temperature between 0° and 40° C.

b) Compounds of general formula I wherein $R^2$ is a group of general formula IV

(wherein $R^9$ is a hydrogen atom or a methyl group and $R^{10}$ denotes a methyl or hydroxymethyl group):

by reacting a compound of general formula II (wherein n, m, A, X, $R^1$ and $R^3$ to $R^7$ are as hereinbefore defined) with an epoxide of general formula V,

wherein $R^9$ and $R^{10}$ are as hereinbefore defined.

The reaction is conveniently carried out in a suitable solvent such as ethanol, tert.butanol, tetrahydrofuran, dimethylformamide or dimethylsulphoxide or in a mixture of the above-mentioned solvents, at temperatures between 0° C. and 100° C., but preferably at a temperature between 0° and 40° C.

c) By reacting compounds of general formula VI

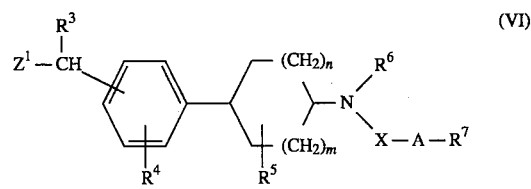

(wherein n, m, A, X and $R^3$ to $R^7$ are as hereinbefore defined, and $Z^1$ denotes a reactive leaving group such as a halogen atom, e.g. a chlorine or bromine atom, or a sulphonyloxy group)

with an amine of general formula VII

$$R^1R^2NH \qquad\qquad (VII)$$

wherein $R^1$ and $R^2$ are as hereinbefore defined.

The reaction is conveniently carried out in a suitable solvent such as ethanol, tert.butanol, tetrahydrofuran, dimethylformamide or dimethylsulphoxide or in a mixture of the above solvents, optionally in the presence of a base such as potassium carbonate, sodium carbonate or a tert.amine which is difficult to alkylate, such as N-ethyldiisopropylamine, at temperatures between 0° C. and 100° C., but preferably at a temperature between 0° and 40° C.

d) By reacting compounds of general formula VIII

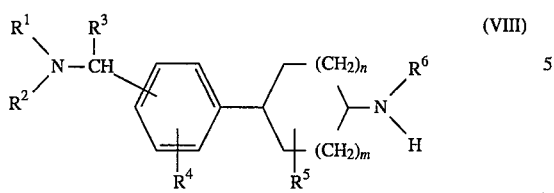

(wherein n, m and $R^1$ to $R^6$ are as hereinbefore defined) with an alkylating agent of general formula IX $$R^7\!-\!A\!-\!X\!-\!Z^2 \qquad (IX)$$

wherein A, X and $R^7$ are as hereinbefore defined and $Z^2$ denotes a reactive leaving group such as a halogen atom, preferably a chlorine atom, or the imidazolide group.

If $Z^2$ denotes a halogen atom, the reactions are carried out in a suitable inert solvent such as diethylether, toluene, methylene chloride and the like, preferably at temperatures between −50° C. and 50° C. and in the presence of a hydrohalic acid-binding agent, e.g. a tertiary amine, sodium carbonate or calcium carbonate. It is possible to use not only the free amines of general formula VIII but also the salts thereof from which the amines may be released in situ using suitable bases, e.g. tertiary organic amines.

If $Z^2$ denotes the imidazolide group, the reactions are preferably carried out in an inert solvent such as xylene or tetrahydrofuran at temperatures between ambient temperature and the boiling temperature of the reaction mixture.

If a compound of general formula VIII has one or two hydroxy groups, the reaction may be modified so as to use two or three equivalents of the compound of general formula IX and, after the reaction has ended, to re-saponify the ester groups formed from the hydroxy groups.

The optional subsequent saponification of an ester group thus formed is preferably carried out by alkaline hydrolysis in an aqueous solvent, e.g. in water, isopropanol/water, tetrahydrofuran/water or dioxane/water, e.g. in the presence of an alkali metal base such as sodium hydroxide or potassium hydroxide, at temperatures between 0° and 100° C.

If according to the invention a compound of general formula I is obtained wherein $R^2$ denotes a hydroxy-substituted alkyl group, this may be converted by reaction with a suitable acylating agent into a compound of general formula I wherein $R^2$ denotes an alkyl group substituted by an alkylcarbonyloxy or alkoxycarbonyloxy group, or it may be converted by oxidation into a compound of general formula I wherein $R^2$ denotes an alkylcarbonylmethyl group.

The subsequent acylation is conveniently carried out in a solvent or mixture of solvents consisting of methylene chloride, chloroform, ether, tetrahydrofuran, dioxane or dimethylformamide, with carboxylic acid anhydrides such as acetic anhydride, with carboxylic acid halides such as acetylchloride or alkylchlorocarbonates, optionally in the presence of an inorganic or tertiary organic base such as potassium carbonate, triethylamine, N-ethyldiisopropylamine or pyridine, whilst the latter three may simultaneously be used as solvent, at temperatures between −25° and 100° C., but preferably at temperatures between −10° and 80° C.

The subsequent oxidation is conveniently carried out in a suitable solvent or mixture of solvents, e.g. in acetone, pyridine, water/pyridine, glacial acetic acid, dichloromethane, chloroform, benzene or toluene at temperatures between −20° and 100° C. The oxidising agents used may be, for example, dimethylsulphoxide in conjunction with N,N-dicyclohexylcarbodiimide and trifluoroacetic acid (oxidation according to Pfitzner-Moffatt), chromic acid in glacial acetic acid or in acetone, manganese dioxide in chloroform or potassium permanganate in glacial acetic acid, pyridine or in acetone.

The compounds of general formula I prepared by the above methods may be purified and isolated by known methods, e.g. crystallisation, distillation or chromatography.

Furthermore, the compounds of general formula I obtained may if desired be converted into the acid addition salts thereof, particularly for pharmaceutical use into the physiologically acceptable salts thereof with inorganic or organic acids. Examples of suitable acids include hydrochloric acid, hydrobromic acid, sulphuric acid, phosphoric acid, fumaric acid, succinic acid, lactic acid, citric acid, tartaric acid or maleic acid.

In the compounds of formula I according to the invention, the aryl group bound to the cycloalkyl ring and the nitrogen atom may be in either an equatorial or axial arrangement. The invention includes both the pure isomers and also mixtures of the different isomers.

Starting Materials

The starting compounds of general formula II may be prepared from compounds of general formula X

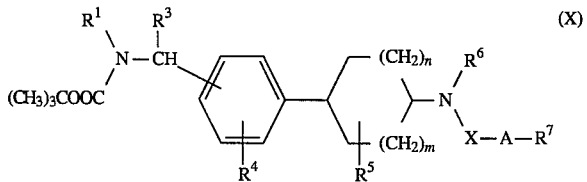

(wherein n, m, A, X, $R^1$ and $R^3$ to $R^7$ are as hereinbefore defined)
by cleaving the tert.butoxycarbonyl group.

The compounds of general formula X may be prepared, starting from ketones of general formula XI

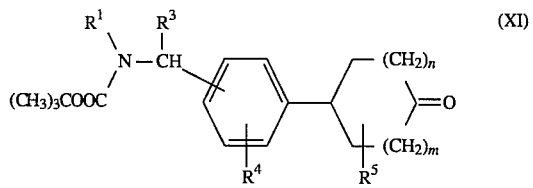

(wherein n, m, $R^1$ and $R^3$ to $R^5$ are as hereinbefore defined) by first reductively aminating these compounds with amines of formula $R^6NH_2$ (wherein $R^6$ is as hereinbefore defined) and then reacting them with an acylating agent of general formula IX $$R^7\!-\!A\!-\!X\!-\!Z^2 \qquad (IX)$$

wherein A, X, $R^7$ and $Z^2$ are as hereinbefore defined.

The ketones of general formula XI may be prepared starting from compounds of formula XII

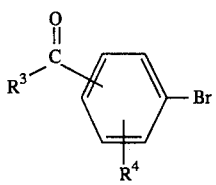 (XII)

(wherein R³ and R⁴ are as hereinbefore defined) by reductive amination with amines of formula $R^1NH_2$ (wherein $R^1$ is as hereinbefore defined) and subsequently reacting the amino group with trimethylchlorosilane, exchanging the bromine atom for lithium, reacting the resulting organolithium compound with compounds of general formula XIII

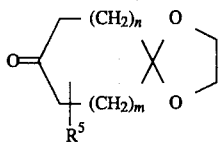 (XIII)

(wherein n, m and $R^5$ are as hereinbefore defined) followed by water cleaving, introducing the tert.butoxycarbonyl group into the amino group, catalytic hydrogenation of the olefinic double bond, e.g. using palladium/barium sulphate as the hydrogenation catalyst, and finally hydrolysing the ethylene ketal.

Starting compounds of general formula VI (wherein $R^3$ and $R^4$ each denote a hydrogen atom, n, m, $R^5$ and X are as hereinbefore defined, $R^6$, $R^7$ and A have the meanings given hereinbefore with the exception of hydrohalic acid-sensitive groups, such as the allyl, propargyl, cyclopropyl, alkenylene or alkynylene group, the group $Z^1$—CH($R^3$)— is in the 4-position relative to the cycloalkyl group and $Z^1$ denotes a chlorine atom) may be prepared by chloromethylation of compounds of general formula XIV

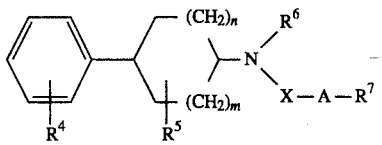 (XIV)

wherein $R^4$ denotes a hydrogen atom, n, m, $R^5$ and X are as hereinbefore defined and $R^6$, $R^7$ and A have the meanings given hereinbefore with the exception of the above-mentioned hydrohalic acid-sensitive groups.

Another method of preparing compounds of general formula VI (wherein n, m, A, X and $R^3$ to $R^7$ are as hereinbefore defined and $Z^1$ denotes a bromine atom or a sulphonyloxy group) consists of converting a compound of general formula XV

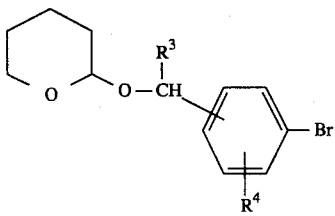 (XV)

(wherein $R^3$ and $R^4$ are as hereinbefore defined) analogously to a reaction sequence described for compounds of formula X above, into compounds of general formula XVI

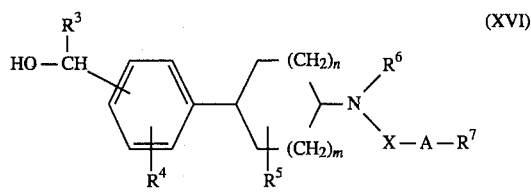 (XVI)

(wherein n, m, A, X and $R^3$ to $R^7$ are as hereinbefore defined) and then converting the hydroxy group into the sulphonyloxy group or substituting it by a bromine atom.

The starting compounds of general formula VIII may be prepared by first producing compounds of general formula XVI (wherein n, m and $R^3$ to $R^6$ are as hereinbefore defined and the group —X—A—$R^7$ is replaced by a tert.butoxycarbonyl group) and converting them via the corresponding sulphonyloxy compounds into compounds of general formula XVII

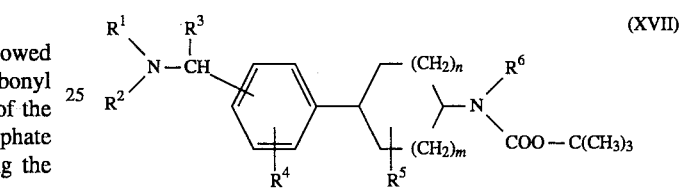 (XVII)

(wherein n, m and $R^1$ to $R^6$ are as hereinbefore defined) followed by cleaving the tert.butoxycarbonyl group.

The starting compounds of general formula XIV may be obtained by first reductively aminating a compound of formula XVIII

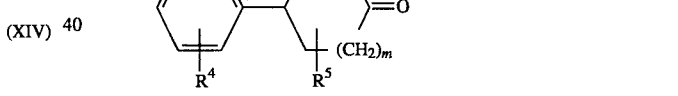 (XVII)

(wherein n, m, $R^4$ and $R^5$ are as hereinbefore defined) with an amine of formula $R^6NH_2$ (wherein $R^6$ is as hereinbefore defined) and subsequently reacting the resulting compound with an acylating agent of general formula IX $$R^7—A—X—Z^2 \quad \text{(IX)}$$

wherein A, X, $R^7$ and $Z^2$ are as hereinbefore defined —

Alternatively, compounds of general formula XIV may first be prepared (wherein n, m, A, X, $R^4$, $R^5$ and $R^7$ are as hereinbefore defined and $R^6$ denotes a hydrogen atom) and these may then be reacted with an alkylating agent of formula $R^6$—Y (wherein $R^6$ has the above meanings, with the exception of a hydrogen atom, and Y is a reactive leaving group such as a halogen atom, e.g. a chlorine, bromine or iodine atom, or a sulphonyloxy group).

The compounds of the general formula I have interesting biological properties. They are inhibitors of cholesterol biosynthesis, in particular inhibitors of the enzyme 2,3-epoxysqualene lanosterol cyclase. On account of their biological properties, they are particularly suitable for the treatment and prophylaxis of hyperlipidaemias, in particular of hypercholesterolaemia, hyperlipoproteinaemia and hypertriglycerideaemia and the atherosclerotic vascular changes resulting therefrom and their sequelae such as coronary heart disease, cerebral ischaemia, intermittent claudication, gangrene and others.

For the treatment of these disorders, the compounds of the general formula I may either be employed on their own for monotherapy or used with other cholesterol- or lipid-lowering substances, wherein the compounds may preferably be administered as an oral formulation, and optionally also in the form of suppositories as a rectal formulation. Possible combination partners in this case are, for example:
- bile acid-binding resins such as e.g. cholestyramine, colestipol, etc.,
- compounds which inhibit cholesterol resorption, such as e.g. sitosterol and neomycin,
- compounds which intervene in cholesterol biosynthesis, such as e.g. HMG-CoA reductase inhibitors such as lovastatin, simvastatin, pravastatin, etc.,
- squalene epoxidase inhibitors such as, for example, NB 598 and analogous compounds and also
- squalene synthetase inhibitors such as, for example, representatives of the isoprenoid-(phosphinylmethyl)-phosphonate class and squalestatin.

Further possible combination partners which may be mentioned are the fibrate class, such as clofibrate, bezafibrate, gemfibrozil, etc., and nicotinic acid, its derivatives and analogues such as, for example, acipimox and probucol.

In addition, the compounds of the general formula I are suitable for the treatment of disorders which are connected with excessive cell proliferation. Cholesterol is an essential cell constituent and must be present in an adequate amount for cell proliferation, i.e. cell division. The inhibition of cell proliferation by inhibition of cholesterol biosynthesis is illustrated by the example of smooth muscle cells with the HMG-CoA reductase inhibitor of the statin type lovastatin, as mentioned at the beginning.

Foremost examples of disorders which are connected with excessive cell proliferation are carcinoses. In cell culture and in in vivo experiments, it has been shown that lowering of the serum cholesterol or intervention in cholesterol biosynthesis by HMG-CoA reductase inhibitors reduces tumour growth (Lancet 339, 1154–1156 [1992]). The compounds of the formula I according to the invention are therefore potentially suitable for the treatment of carcinoses on account of their cholesterol biosynthesis-inhibitory activity. They may be used for this purpose on their own or to support known therapy principles.

Further examples which may be mentioned are hyperproliferative skin disorders such as, for example, psoriasis, basal cell carcinoma, squamous cell carcinoma, keratosis and keratinization disorders. The expression "psoriasis" used here, signifies a hyperproliferative-inflammatory skin disorder which changes the regulatory mechanism of the skin. In particular, lesions are formed which include primary and secondary changes of proliferation in the epidermis, inflammatory reactions of the skin and the expression of regulatory molecules such as lymphokines and inflammation factors. Psoriatic skin is morphologically characterized by an increased turnover of epidermis cells, thickened epidermis, abnormal keratinization of inflammatory cell infiltrates into the dermis layer and polymorphonuclear leucocyte infiltration into the epidermis, which causes an increase in the basal cell cycle. Hyperkeratotic and parakeratotic cells are also present. The expressions "keratosis", "basal cell carcinoma", "squamous cell carcinoma" and "keratinization disorders" relate to hyperproliferative skin disorders in which the regulatory mechanism for the proliferation and differentiation of the skin cells is interrupted.

The compounds of the formula I are active as antagonists of skin hyperproliferation, i.e. as agents which inhibit the hyperproliferation of human keratinocytes. As a result of this, the compounds are suitable as agents for the treatment of hyperproliferative skin disorders such as psoriasis, basal cell carcinomas, keratinization disorders and keratosis. For the treatment of these disorders, the compounds of the formula I may be administered either orally or topically, and they may be used either on their own in a form of monotherapy or in combination with known active compounds.

Further noteworthy examples are hyperproliferative vascular disorders such as stenoses and vascular occlusions caused by surgical measures such as PTCA (percutaneous transluminal coronary angioplasty) or bypass operations, which are based on the proliferation of smooth muscle cells. As mentioned at the beginning, it is known that this cell proliferation can be suppressed by HMG-CoA reductase inhibitors of the statin type, such as lovastatin. On account of their inhibitory effect on cholesterol biosynthesis, the compounds of the general formula I are also suitable for the treatment and prophylaxis of these disorders, where they may either be used on their own or in combination with known active compounds, such as e.g. intravenously administered heparin, preferably in oral administration.

A further possible use of the compounds of the general formula I according to the invention is the prophylaxis and treatment of gallstone trouble. The formation of gallstones is caused by the cholesterol concentration in the bile exceeding the maximum solubility of cholesterol in the bile fluid, causing precipitation of the cholesterol in the form of gallstones. Hypolypidaemic agents of the fibrate class lead to an increased secretion of neutral steroids via the bile and increase the susceptibility to gallstone formation.

In contrast to this, cholesterol biosynthesis inhibitors such as lovastatin or pravastatin do not lead to increased gallstone formation, but can cause a reduction of the cholesterol concentration in the bile and thus reduce the so-called lithogenic index, a measure of the probability of gallstone formation. This is described in Gut 31, 348–350 [1990] and in Z. Gastroenterol. 29, 242–245 [1991].

Moreover, the effectiveness of lovastatin in the disolution of gallstones, in particular in combination with ursodeoxycholic acid, is described in Gastroenterology 102, No. 4, Pt. 2, A 319 [1992]. On account of their mode of action, the compounds of the general formula I are therefore also of importance for the prophylaxis and treatment of gallstone trouble. They may be used either on their own or in combination with known therapies such as, for example, treatment with ursodeoxycholic acid or shock wave lithotripsy, preferably by oral administration.

Finally, the compounds of the general formula I are suitable for the therapy of infections due to pathogenic fungi such as e.g. *Candida albicans, Aspergillus niger, Trichophyton mentagrophytes,* Penicillium sp., Cladosporium sp., etc. As previously mentioned, the final product of sterol biosynthesis in the fungal organism is not cholesterol, but ergosterol which is essential for the integrity and function of the fungal cell membranes. The inhibition of ergosterol biosynthesis therefore leads to growth disorders and possibly to the destruction of the fungal organisms.

For the treatment of mycoses, the compounds of the general formula I may either be administered orally or topically. They may be employed either on their own or in combination with known antimycotic active compounds, in particular with those which intervene in other stages of sterol biosynthesis, such as, for example, the squalene epoxidase inhibitors terbinafine and naftifine or the lanosterol 14α-demethylase inhibitors of the azole type such as, for example, ketoconazole and fluconazole.

A further possible use of the compounds of the general formula I relates to an application in raising poultry. The lowering of the cholesterol content of eggs by administration of the HMG-CoA reductase inhibitor lovastatin in laying hens has been described (FASEB Journal 4, A 533, Abstracts 1543 [1990]). The production of low-cholesterol eggs is of interest, since the cholesterol loading of the body may be decreased, without a change in feeding habits, by eggs with a reduced cholesterol content. As a result of their inhibitory effect on cholesterol biosynthesis, the compounds of the general formula I may also be used in poultry breeding for the production of low-cholesterol eggs, the substances preferably being administered to the feed as additives.

The biological activity of compounds of the general formula I was determined by the following methods:

I. Measurement of the inhibition of $^{14}$C-acetate incorporation in digitonin-precipitatable steroids:

Method

After 3 days of culture, human hepatoma cells (HEP-G2) are stimulated for 16 hours in cholesterol-free medium.

The substances to be tested (dissolved in dimethyl sulphoxide, final concentration 0.1%) are added during this stimulation phase. After the addition of 200 μmol/l of 2-$^{14}$C-acetate, the mixture is then reincubated at 37° C. for a further 2 hours.

The cells are detached and the sterol esters are hydrolyzed and, after extraction, sterols are precipitated using digitonin. The $^{14}$C-acetate incorporated into digitonin-precipitatable sterols is determined by scintillation measurement.

The inhibitory effect was investigated at test concentrations of $10^{-7}$ Mol/l and $10^{-8}$ Mol/l. It was found that, for example, the following compounds A to Q of general formula I show a good inhibitory effect at these test concentrations, e.g. an inhibitory effect of at least 50% at a test concentration of $10^{-7}$ mol/l:

A=trans-N-(4-chlorobenzenesulphonyl)-N-methyl-4-[ 4-(2-methoxyethyl)methylaminomethylphenyl]-cyclohexylamine B=trans-4-(4-aminocarbonylmethyl-methylaminomethylphenyl)-N-( 4-chlorobenzenesulphonyl)-N-methylcyclohexylamine C=trans-4-(4-aminocarbonylmethyl-methylaminomethylphenyl)-N-( 4-chlorobenzoyl)-N-methylcyclohexylamine D=trans-N-(4-chlorobenzoyl)-N-methyl-4-[4-( 3-hydroxypropyl)methylaminomethylphenyl]-cyclohexylamine E=trans-4-[4-(3-acetoxypropyl)methylaminomethyl-phenyl]-N-( 4-chlorobenzoyl)-N-methylcyclohexylamine F=trans-N-(4-chlorobenzoyl)-N-methyl-4-[4-( 3-cyanopropyl)-methylaminomethylphenyl]-cyclohexylamine G=trans-4-[4-( 1-aminocarbonylethyl)methylaminomethyl-phenyl]-N-( 4-chlorobenzoyl)-N-methylcyclohexylamine H=trans-N-(4-chlorobenzoyl)-N-methyl-4-[4-(R- 2,3-dihydroxy-2-methylpropyl)methylaminomethylphenyl]-cyclohexylamine I=trans-N-(4-chlorobenzoyl)-N-methyl-4-[4-( 2-hydroxyethyl)isopropylaminomethylphenyl]cyclohexylamine K=cis-N-(4-chlorobenzoyl)-N-methyl-4-[4-( 3-hydroxypropyl)methylaminomethylphenyl]cyclohexylamine L=trans-4-[4-(3-hydroxypropyl)methylaminomethylphenyl]-N-methyl-N-( 4-trifluoromethylbenzoyl)-cyclohexylamine M=trans-N-cyclohexylcarbonyl-N-methyl-4-[4-( 3-hydroxypropyl)methylaminomethylphenyl]-cyclohexylamine N=trans-N-(4-chloro-3-methylbenzoyl)-N-methyl-4-[ 4-(3-hydroxypropyl)methylaminomethylphenyl]-cyclohexylamine O=trans-N-(3,4-dichlorophenylacetyl)-N-methyl-4-[ 4-(3-hydroxypropyl)methylaminomethylphenyl]-cyclohexylamine P=trans-4-[4-( 3-hydroxypropyl)methylaminomethylphenyl]-N-methyl-N-(1,2,3,4-tetrahydronaphthalene- 2-carbonyl)-cyclohexylamine Q=trans-N-(5-chlorothienyl-2-carbonyl)-N-methyl-4-[ 4-(3-hydroxypropyl)methylaminomethylphenyl]-cyclohexylamine The percentages by which the above compounds inhibit the incorporation of $^{14}$C-acetate are shown in the following Table:

| Mol/l | $10^{-7}$ | $10^{-8}$ |
|---|---|---|
| A | −88 | −80 |
| B | −82 | −77 |
| C | −77 | −36 |
| D | −77 | −47 |
| E | −75 | −40 |
| F | −82 | −61 |
| G | −86 | −61 |
| H | −88 | −58 |
| I | −87 | −60 |
| K | −76 | −35 |
| L | −83 | −50 |
| M | −77 | −41 |
| N | −78 | −40 |
| O | −77 | −49 |
| P | −73 | −37 |
| Q | −80 | −62 |

As mentioned previously, inhibitors of the enzyme 2,3-epoxysqualene-lanosterol cyclase are occasionally described in the literature, however, in terms of their structure these differ very greatly from the compounds of the formula I according to the invention. The compounds structurally most closely related to the compounds of the general formula I are described in EP 0468457. For comparison, therefore, Example 1 of this publication was tested by the determination method described above with test concentrations of $10^{-5}$ mol/l and $10^{-6}$ mol/l. The inhibitory values of 41% and 13% found here, show that these compounds are clearly inferior to the compounds of the general formula I according to the invention.

II. Measurement of the in vivo effect in the rat after oral administration

The inhibition of the enzyme 2,3-epoxysqualene-anosterol cyclase causes an increase in the 2,3-epoxy-squalene level in the liver and plasma. Therefore, the amount of 2,3-epoxysqualene formed therefore serves as a direct measure of the effectiveness in the whole animal. The determination is carried out by the following method:

The test substance suspended in 1.5 % strength aqueous methylcellulose is administered via stomach tube to male Wistar rats (160–190 g body weight). 5 hours after administration, blood is obtained retroorbitally from the venous plexus. Plasma is extracted by the method of Bligh and Dyer (Canad. J. Biochem. Physiol. 37, 912, [1959]), purified by means of a precolumn and then analyzed by means of HPLC. The peaks obtained are identified and quantified by means of calibration substances. An internal standard is used to check the reproducibility of the results.

The investigations were carried out using concentrations of 0.1 and 1.0 mg/kg. The results for the above mentioned substances A to I are compiled in the following Table by way of example:

| Concentration of 2,3-epoxysqualene (µg/ml) in the plasma (rat) | | |
|---|---|---|
| mg/kg | 0.1 | 1.0 |
| A | 1.35 | 4.55 |
| B | 1.28 | 4.83 |
| C | 0.75 | 3.01 |
| D | 0.71 | 4.11 |
| E | 1.01 | 4.37 |
| F | 0.73 | 3.07 |
| G | 0.41 | 1.42 |
| H | 0.79 | 1.46 |
| I | 1.50 | 1.71 |

Measurable 2,3-epoxysqualene levels did not occur in the control animals under the experimental conditions.

To date, none of the inhibitors of the enzyme 2,3-epoxysqualene-lanosterol cyclase as described in the literature have been attributed with inhibitory activity against cholesterol biosynthesis in the whole animal.

III. Lipid reduction in the normolipaemic golden hamster

Male golden hamsters are fed ad lib with a cholesterol-free hamster diet for 12 days. The substance to be tested is admixed to the feed in concentrations of 0.01 to 0.10%. At the end of the experimental period, the total cholesterol, the HDL fraction and also the VLDL+LDL fraction are determined by standard methods, a control group fed without test substance being used for comparison.

The hypolipidaemic activity of the above mentioned compound A was tested. The results are compiled in the following Table:

| Concentration | Total cholesterol | VLDL + LDL | HDL |
|---|---|---|---|
| 0.01% | −21.8% | −28.8% | −17.3% |
| 0.03% | −28.6% | −42.9% | −23.6% |
| 0.10% | −35.1% | −42.5% | −30.6.% |

The compounds A to I appeared to be non-toxic at the curative dose. For example, the compounds D and H showed no toxic effects in the mouse after oral administration of 100 mg/kg, once daily for 4 days.

For pharmaceutical use, the compounds of the general formula I may be incorporated into the customary pharmaceutical preparation forms for oral, rectal and topical administration in a manner known per se.

Formulations for oral administration include, for example, tablets, coated tablets and capsules. For rectal administration suppositories are preferred. The daily dose is between 1 and 1200 mg for a human of 60 kg body weight, but a daily dose of 5 to 100 mg for a human of 60 kg body weight is preferred. The daily dose is preferably divided into 1 to 3 individual doses.

In the case of topical use, the compounds may be administered in preparations which contain approximately 1 to 1000 mg, in particular 10 to 300 mg, of active compound per day. The daily dose is preferably divided into 1 to 3 individual doses.

Topical formulations include gels, creams, lotions, ointments, powders, aerosols and other conventional formulations for the application of medicaments to the skin. The amount of active compound for topical application is 1 to 50 mg per gram of formulation, but preferably 5 to 20 mg per gram of formulation. In addition to application to the skin, the topical formulations of the present invention may also be used in the treatment of mucous membranes which are accessible to topical treatment. For example, the topical formulations may be applied to the mucous membranes of the mouth, the lower colon, etc.

For use in poultry breeding to produce low-cholesterol eggs, the active compounds of the general formula I are administered to the animals by the customary methods as an additive to suitable foodstuffs. The concentration of the active compounds in the finished feed is normally 0.01 to 1%, but preferably 0.05 to 0.5%.

The active compounds may be added to the feed as such. In addition to the active compound and optionally in addition to a customary vitamin/mineral mixture, the foodstuffs for laying hens according to the invention may thus contain, for example, maize, soya bean flour, meat meal, feed fat and soya oil. One of the compounds of the formula I mentioned above is admixed to this feed as an active compound in a concentration of 0.01 to 1%, but preferably 0.05 to 0.5%.

The Examples which follow serve to illustrate the invention. The $R_f$ values specified were determined on prepared plates obtained from E. Merck of Darmstadt, more specifically on:

a) alumina F-254 (Type E)
b) silica gel 60 F-254.

Examples of the preparation of the starting materials

EXAMPLE A 4-(4-tert. Butoxycarbonyl-methylaminomethylphenyl)-cyclohexanone 800 ml of an 8% solution of methylamine in toluene are added, whilst cooling with ice, to 100 g of 4-bromobenzaldehyde and 300 g of molecular sieve (3 Angstroms). The mixture is stirred overnight at ambient temperature, suction filtered to remove the molecular sieve and the solvent is evaporated off. The residue is dissolved in 1.4 litres of ice cold methanol and 48 g of sodium borohydride are added in batches whilst cooling with ice. Then the mixture is stirred for 30 minutes at 0° C., for one hour at 10° C. and for two hours at ambient temperature, then evaporated to dryness, the residue is taken up in ice water, acidified with half concentrated hydrochloric acid and extracted twice with ether. The ether is discarded, the aqueous phase is made alkaline with concentrated sodium hydroxide solution whilst cooling and then extracted three times with ether. The organic phase is washed with water and saturated saline solution, dried and evaporated down. 96.8 g of N-methyl-4-bromobenzylamine are obtained in the form of a colourless oil.

This product is dissolved in 466 ml of anhydrous tetrahydrofuran and, at −15° to −20° C., 300 ml of a 1.6 M solution of n-butyllithium in hexane are added dropwise. Immediately afterwards, at the same temperature, 52.5 g of trimethylchlorosilane are added dropwise and the resulting mixture is stirred for 10 minutes. Then, at −75° to −65° C., a further 320 ml of the above-mentioned n-butyllithium solution are added dropwise, the mixture is stirred for a further 20 minutes at −75° C. and then, at −75° to −65° C., a solution of 76 g of 1,4-cyclohexandione-monoethyleneketal in 225 ml of anhydrous tetrahydrofuran is added dropwise. After 30 minutes' stirring at this temperature the mixture is allowed to return to ambient temperature, then poured into water and extracted three times with ethyl acetate. The organic phase is washed with water and saturated saline solution, dried and evaporated down. The residue is crystallised from ether. 87.1 g of 4-hydroxy-4-( 4-methylaminomethyl-phenyl)-cyclohexanone-ethylene-ketal with a melting point of 98°–100° C. are obtained.

This product is refluxed together with 65.7 g of p-toluenesulphonic acid in 1200 ml of toluene and 200 ml of ethylene glycol using a water separator until the water separation ceases (about 2.5 hours), then cooled and the solution is diluted with ethyl acetate. It is washed with sodium hydroxide solution, water and saturated saline solution, dried and evaporated down. The oily residue is dissolved in 700 ml of anhydrous tetrahydrofuran, 75 g of di-tert.butylpyrocarbonate are added in batches and the mixture is stirred for two hours at ambient temperature. The solvent is evaporated off, the residue is dissolved in ether, washed with water, dried and the ether is evaporated off. 122 g of 4-(4-tert.butoxycarbonyl-methylaminomethylphenyl)-cyclohex-3-enone-ethyleneketal are obtained in the form of a colourless oil.

This product is dissolved in a mixture of 400 ml of methanol and 400 ml of ethyl acetate and hydrogenated in the presence of 15 g of palladium/barium sulphate at ambient temperature under 5 bars of hydrogen pressure. The catalyst is filtered off and the solvent is evaporated off. The residue is recrystallised from diisopropylether at low temperature. 88 g of 4-( 4-tert.butoxycarbonyl-methylaminomethylphenyl)-cyclohexanone-ethyleneketal are obtained, melting point 117°–118° C.

47.5 g of this product are refluxed for 16 hours together with 900 ml of acetone, 90 ml of water and 4.5 g of pyridinium-p-toluenesulphonate. After cooling and the addition of water the acetone is evaporated off and the aqueous mixture is combined with ethyl acetate. The organic phase is extracted twice with water, washed with saturated saline solution, dried and evaporated down. After recrystallisation from petroleum ether, 34 g of the title compound are obtained, m.p. 62°–64° C.

The following were obtained in the same way:

a) 4-(3-tert.butoxycarbonyl-methylaminomethylphenyl)-cyclohexanone from 3-bromobenzaldehyde, methylamine and 1,4-cyclohexanedione-monoethyleneketal. Colourless oil. $R_f$ value: 0.38 (silica gel, petroleum ether/ethyl acetate 3:1, v:v).

b) 4-[4-(1-tert.butoxycarbonyl-methylaminoethyl)phenyl]-cyclohexanone from 4-bromoacetophenone, methylamine and 1,4-cyclohexanedione-monoethyleneketal. Oil. $R_f$ value: 0.35 (silica gel, petroleum ether/ethyl acetate 3:1, v:v).

EXAMPLE B 4-(4-Hydroxymethylphenyl)cyclohexanone

In order to protect the hydroxy group, first of all 31 g (0,166 Mol) of 4-bromobenzylalcohol are converted into the corresponding tetrahydropyranylether by methods known from the literature by reacting with dihydropyran (200 ml tetrahydrofuran, 50 ml 1,2-dihydropyran, catalytic amount of p-toluenesulphonic acid, 48 hours' stirring at ambient temperature). The product obtained is reacted, as described in Example A, with n-butyllithium and 1,4-cyclohexanedione monoethyleneketal. 58 g (81% of theory) of 4-hydroxy-4-[4-( 2-pyranyloxymethylphenyl)cyclohexanone-ethyleneketal are obtained, melting point 99°–101° C.

3.5 g of this product in 30 ml of pyridine are combined with 2.2 ml of thionylchloride, whilst cooling with ice. The resulting oil (2.7 g), which is a mixture of two substances, is hydrogenated in a mixture of 40 ml of ethyl acetate and 20 ml of methanol in the presence of 1.5 g of palladium/calcium carbonate at ambient temperature under a hydrogen pressure of 5 bar. The resulting oil (2.4 g) is refluxed overnight in 40 ml of acetone and 10 ml of water with 0.2 g of pyridinium-p-toluenesulphonate. The crude product is purified by column chromatography (silica gel, ethyl acetate/petroleum ether=1:1, v:v). 1.0 g of the title compound is obtained, melting point 58°–60° C.

EXAMPLE C cis- and trans-4-(4-tert. Butoxycarbonyl-methylaminomethylphenyl)-N-methylcyclohexylamine 6.3 g (0.02 mol) of 4-(4-tert.butoxycarbonyl-methylaminomethylphenyl)cyclohexanone are reacted with methylamine and sodium borohydride in the manner described in Example A for 4-bromobenzaldehyde. The product obtained is purified by column chromatography (aluminium oxide, ethyl acetate/methanol=20:1 to 1:1, v:v). First, a small amount of the cis-isomer is obtained as a colourless oil. $R_f$ value: 0.56 (alumina, ethyl acetate/methanol=24:1, v:v).

Then, as a further fraction, 4.0 g (60.2% of theory) of the trans-isomer of the title compound are obtained in the form of a colourless oil. $R_f$ value: 0.34 (alumina, ethyl acetate/methanol=24:1, v:v) .

The following were obtained in the same way:

a) trans-4-(4-tert.butoxycarbonyl-methylaminomethylphenyl)-N-cyclopropylcyclohexylamine from 4-(4-tert.butoxycarbonyl-methylaminomethylphenyl)-cyclohexanone and cyclopropylamine. Colourless oil. $R_f$ value: 0.51 (alumina, petroleum ether/ethyl acetate=4:1, v:v).

b) trans-N-allyl-4-(4-tert.butoxycarbonyl-methylaminomethylphenyl)cyclohexylamine from 4-(4-tert.butoxycarbonyl-methylaminomethylphenyl)-cyclohexanone and allylamine. Colourless oil. $R_f$ value: 0.52 (alumina, petroleum ether/ethyl acetate=3:1, v:v).

c) trans-4-(4-tert.butoxycarbonyl-methylaminomethylphenyl)-N-propargylcyclohexylamine from 4-(4-tert.butoxycarbonyl-methylaminomethylphenyl)-cyclohexanone and progargylamine. Colourless oil. $R_f$ value: 0.39 (alumina, petroleum ether/ethyl acetate=3:1, v:v).

d) trans-4-[4-(1-tert.butoxycarbonyl-methylaminoethyl)-phenyl]-N-methylcyclohexylamine from 4-[4-(1-tert.butoxycarbonyl-methylaminoethyl)-phenyl]-cyclohexanone and methylamine. Oil. $R_f$ value: 0.5 (alumina, ethyl acetate/methanol=10:1, v:v).

e) trans-4-(3-tert.butoxycarbonyl-methylaminomethylphenyl)-N-methylcyclohexylamine from 4-(3-tert.butoxycarbonyl-methylaminomethylphenyl)-cyclohexanone and methylamine. Colourless oil.

f) trans-N-methyl-4-phenylcyclohexylamine from 4-phenylcyclohexanone and methylamine. Melting point: 40° C.

g) trans-N-cyclohexyl-4-phenylcyclohexylamine from 4-phenylcyclohexanone and cyclohexylamine. Melting point: 68°–70° C.

h) trans-N-isopropyl-4-phenylcyclohexylamine from 4-phenylcyclohexanone and isopropylamine. Melting point: 61°–63° C.

i) trans-N-hexyl-4-phenylcyclohexylamine from 4-phenylcyclohexanone and hexylamine. Colourless oil. $R_f$ value: 0.25 (alumina, petroleum ether/ethyl acetate 9:1, v:v).

j) trans-N-neopentyl-4-phenylcyclohexylamine from 4-phenylcyclohexanone and neopentylamine. Colourless oil.

k) trans-4-(4-hydroxymethylphenyl)-N-methylcyclohexylamine from 4-(4-hydroxymethylphenyl)cyclohexanone and methylamine. Melting point: 131°–134° C.

l) trans-4-phenylcyclohexylamine from 4-phenylcyclohexanone and benzylamine, followed by catalytic removal of the N-benzyl group (palladium/charcoal). Melting point: sintering from 46°–48° C.

m) trans-4-(4-tert.butoxycarbonyl-methylaminomethylphenyl)-N-ethylcyclohexylamine from 4-(4-tert.butoxycarbonyl-methylaminomethyl-phenyl)cyclohexanone and ethylamine. Colourless oil. $R_f$ value: 0.45 (alumina, petroleum ether/ethyl acetate= 1:1, v:v).

n) trans-N-benzyl-4-(4-tert.butoxycarbonyl-methylaminomethylphenyl)cyclohexylamine from 4-(4-tert.butoxycarbonyl-methylaminomethylphenyl)-cyclohexanone and benzylamine. Colourless oil. $R_f$ value: 0.45 (alumina, petroleum ether/ethyl acetate= 2:1, v:v).

o) trans-4-(4-tert.butoxycarbonyl-methylaminomethylphenyl)-N-( 4-fluorobenzyl)cyclohexylamine from 4-(4-tert.butoxycarbonyl-methylaminomethylphenyl)-cyclohexanone and 4-fluorobenzylamine. Colourless oil. $R_f$ value: 0.43 (alumina, petroleum ether/ethyl acetate= 5:1, v:v).

EXAMPLE D trans-4-(4-tert. Butoxycarbonyl-methylaminomethylphenyl)-N-( 4-chlorobenzoyl)-N-methylcyclohexylamine 8 g (0.024 Mol) of trans-4-( 4-tert.butoxycarbonyl-methylaminomethylphenyl)-N-methylcyclohexylamine are reacted in 300 ml of ether with 4.6 g (0.026 Mol) of 4-chlorobenzoylchloride in the presence of 2.7 g (0.026 Mol) of triethylamine. 10.3 g of the title compound are obtained, melting point 152°–154° C.

The following were prepared in the same way:

a) trans-4-(4-tert.butoxycarbonyl-methylaminomethylphenyl)-N-( 4-chlorobenzoyl)-N-cyclopropylcyclohexylamine from trans-4-(4-tert.butoxycarbonyl-methylaminomethylphenyl)-N-cyclopropylcyclohexylamine and 4-chlorobenzoyl chloride. Melting point: 151°–152° C.

b) trans-N-allyl-N-(4-chlorobenzoyl)-4-( 4-tert.butoxycarbonylmethylaminomethylphenyl)-cyclohexylamine from trans-N-allyl-4-(4-tert.butoxy-carbonylmethylaminomethylphenyl)cyclohexylamine and 4-chlorobenzoylchloride. Colourless oil. $R_f$ value: 0.43 (alumina, petroleum ether/ethyl acetate=2:1, v:v).

c) trans-4-(4-tert.butoxycarbonyl-methylaminomethylphenyl)-N-( 4-chlorobenzoyl)-N-propargylcyclohexylamine from trans-4-(4-tert.butoxycarbonyl-methylaminomethylphenyl)-N-propargylcyclohexylamine and 4-chlorobenzoylchloride. Colourless oil. $R_f$ value: 0.46 (silica gel, petroleum ether/ethyl acetate= 2:1, v:v).

d) trans-4-[4-(1-tert.butoxycarbonyl-methylaminoethyl)-phenyl]-N-( 4-chlorobenzoyl)-N-methylcyclohexylamine from trans-4-[4-(1-tert.butoxycarbonyl-methylaminoethyl)-phenyl]-N-methylcyclohexylamine and 4-chlorobenzoylchloride. Melting point: 172°–174° C.

e) trans-4-(3-tert.butoxycarbonyl-methylaminomethylphenyl)-N-( 4-chlorobenzoyl)-N-methylcyclohexylamine from trans-4-(3-tert.butoxycarbonyl-methylaminomethylphenyl)-N-methylcyclohexylamine and 4-chlorobenzoylchloride. Melting point: 134°–135° C.

f) trans-N-(4-chlorobenzoyl)-N-methyl- 4-phenylcyclohexylamine from trans-N-methyl-4-phenylcyclohexylamine and 4-chlorobenzoylchloride. Melting point: 138°–140° C.

g) trans-N-(4-chlorobenzoyl)-N-cyclohexyl- 4-phenylcyclohexylamine from trans-N-cyclohexyl-4-phenylcyclohexylamine and 4-chlorobenzoylchloride. Melting point: 164°–166° C.

h) trans-N-(4-chlorobenzoyl)-N-isopropyl- 4-phenylcyclohexylamine from trans-N-isopropyl-4-phenylcyclohexylamine and 4-chlorobenzoylchloride. Melting point: 130°–132° C.

i) trans-N-(4-chlorobenzoyl)-N-hexyl-4-phenylcyclohexylamine from trans-N-hexyl-4-phenylcyclohexylamine and 4-chlorobenzoylchloride. Melting point: 105° C.

j) trans-N-(4-chlorobenzoyl)-N-neopentyl-4-phenylcyclohexylamine from trans-N-neopentyl-4-phenylcyclohexylamine and 4-chlorobenzoylchloride Colourless crystals.

k) trans-N- (4-chlorobenzoyl) -N-methyl-4- ( 4-hydroxymethylphenyl)cyclohexylamine from trans-4-(4-hydroxymethylphenyl)-N-methylcyclohexylamine and 4-chlorobenzoylchloride. Melting point: 211°–213° C.

l) trans-N-(4-chlorobenzoyl)-4-phenylcyclohexylamine from trans-4-phenylcyclohexylamine and 4-chlorobenzoylchloride. Melting point: 232°–234° C.

m) trans-4-(4-tert.butoxycarbonyl-methylaminomethylphenyl)-N-( 4-chlorobenzenesulphonyl)-N-methylcyclohexylamine from trans-4-(4-tert.butoxycarbonyl-methylaminomethylphenyl)-N-methylcyclohexylamine and 4-chlorobenzenesulphonic acid chloride. Melting point: 105°–106° C.

n) trans-N-acetyl-N-benzyl-4-( 4-tert.butoxycarbonylmethylaminomethylphenyl)cyclohexylamine from trans-N-benzyl-4-(4-tert.butoxycarbonyl-methylaminomethylphenyl)cyclohexylamine and acetylchloride. Oil. $R_f$ value: 0.66 (alumina, ethyl acetate/petroleum ether= 1:3, v:v).

o) trans-N-acetyl-N-(4-fluorobenzyl)-4-(4-tert.butoxycarbonyl-methylaminomethylphenyl)-cyclohexylamine from trans-4-(4-tert.butoxycarbonyl-methylaminomethylphenyl)-N-( 4-fluorobenzyl)-cyclohexylamine and acetylchloride. Colourless oil.

p) trans-4-(4-tert.butoxycarbonyl-methylaminomethylphenyl)-N-( 4-fluorobenzyl)-N-methanesulphonylcyclohexylamine from trans-4-(4-tert.butoxycarbonyl-methylaminomethylphenyl)-N-( 4-fluorobenzyl)cyclohexylamine and methanesulphonic acid chloride. Colourless oil.

q) trans-4-(4-tert.butoxycarbonyl-methylaminomethylphenyl)-N-methyl-N-(4-phenyl- 3-butenoyl)cyclohexylamine from trans-4-(4-tert.butoxycarbonyl-methylaminomethylphenyl)-N-methylcyclohexylamine and 4-phenyl-3-butenoylchloride. Colourless oil. $R_f$ value: 0.5 (silica gel, petroleum ether/ethyl acetate=1:1, v:v).

r) trans-4-(4-tert.butoxycarbonyl-methylaminomethylphenyl)-N-ethyl-N-( 4-phenyl-3butenoyl)cyclohexylamine from trans-4-(4-tert.butoxycarbonyl-methylaminomethylphenyl)-N-ethylcyclohexylamine and 4-phenyl-3-butenoylchloride. Colourless oil. $R_f$ value: 0.74 (alumina, petroleum ether/ethyl acetate=2:1, v:v).

s) trans-N-benzyl-N-(4-phenyl-3-butenoyl)-4-( 4-tert.butoxycarbonyl-methylaminomethylphenyl)-cyclohexylamine from trans-N-benzyl-4-(4-tert.butoxycarbonyl-methylaminomethylphenyl)cyclohexylamine and 4-phenyl-3-butenoylchloride. Colourless oil. $R_f$ value: 0.26 (alumina, petroleum ether/ethyl acetate/methanol=10:10:1, v:v:v).

t) cis-4-(4-tert.butoxycarbonylmethylamino-methylphenyl)-N-( 4-chlorobenzoyl)-N-methylcyclohexylamine from cis-4-(4-tert.butoxycarbonyl-methylaminomethylphenyl)-N-methylcyclohexylamine and 4-chlorobenzoylchloride. Melting point: 98°–100° C.

u) trans-4-(4-tert.butoxycarbonyl-methylaminomethylphenyl)-N-hexanoyl-N-methylcyclohexylamine from trans-4-(4-tert.butoxycarbonyl-methylaminomethylphenyl)-N-methylcyclohexylamine and hexanoic acid chloride. Melting point: 83°–85° C.

v) trans-4-[4-(1-tert.butoxycarbonyl-methylaminoethyl)-phenyl]-N-( 4-chlorobenzenesulphonyl)-N-methylcyclohexylamine from trans-4-[4-( 1-tert.butoxycarbonyl-methylaminoethyl)-phenyl]-N-methylcyclohexylamine and 4-chlorobenzenesulphonic acid chloride. Melting point: 55° C.

EXAMPLE E trans-N-tert. Butoxycarbonyl-N-methyl-4-(4-hydroxymethylphenyl)cyclohexylamine 15.3 g of trans-4-(4-hydroxymethylphenyl)-N-methylcyclohexylamine are reacted in 250 ml of tetrahydrofuran with 16.7 g of di-tert.-butyl pyrocarbonate. 17.7 g of the title compound are obtained, melting point 111°–113° C.

EXAMPLE F trans-N-(4-Chlorobenzoyl)-N-ethyl-4-phenylcyclohexylamine 1 g of trans-N-(4-chlorobenzoyl)-4-phenylcyclohexylamine in 20 ml of dimethylformamide are mixed with 0.14 g of 55% sodium hydride and after 15 minutes 0.62 g of ethyliodide are added. After 1 hour at ambient temperature the reaction solution is evaporated down, the residue is taken up in water, extracted with ethyl acetate and the organic phase is dried and evaporated down. After purification by column chromatography (silica gel, petroleum ether/ethyl acetate=4:1 to 3:1, v:v), 0.73 g of the title compound are obtained, melting point 127°–129° C.

EXAMPLE G trans-N-(4-Chlorobenzoyl)-N-methyl-4-(4-chloromethylphenyl)-cyclohexylamine 33.8 g of trans-N-(4-chlorobenzoyl)-N-methyl-4-phenylcyclohexylamine, 24.3 g of paraformaldehyde and 24.3 g of zinc chloride are suspended in 1300 ml of methylene chloride at ambient temperature and over a period of 2.5 hours hydrogen chloride is introduced, whilst the temperature rises to 29° C. The solution obtained is stirred overnight, poured into 1500 ml of ice water and then stirred until phase separation is obtained. The organic phase is washed with water, dried and concentrated by evaporation and the residue is recrystallised from ethyl acetate. 30.1 g of the title compound, melting point 174°–176° C., are obtained.

The following were obtained in the same way:

a) trans-N-(4-chlorobenzoyl)-N-cyclohexyl-4-(4-chloromethylphenyl)cyclohexylamine from trans-N-(4-chlorobenzoyl)-N-cyclohexyl-4-phenylcyclohexylamine and paraformaldehyde. Melting point: 205°–209° C.

b) trans-N-(4-chlorobenzoyl)-N-isopropyl-4-( 4-chloromethylphenyl)cyclohexylamine from trans-N-(4-chlorobenzoyl)-N-isopropyl-4-phenylcyclohexylamine and paraformaldehyde. Melting point: 160°–163° C.

c) trans-N-(4-chlorobenzoyl)-N-hexyl-4-(4-chloromethylphenyl)-cyclohexylamine from trans-N-(4-chlorobenzoyl)-N-hexyl-4-phenylcyclohexylamine and paraformaldehyde. Melting point: 119° C.

d) trans-N-(4-chlorobenzoyl)-N-neopentyl-4-( 4-chloromethylphenyl)cyclohexylamine from trans-N-(4-chlorobenzoyl)-N-neopentyl-4-phenylcyclohexylamine and paraformaldehyde. $R_f$ value: 0.49 (silica gel, petroleum ether/ethyl acetate= 4:1, v:v).

e) trans-N-(4-chlorobenzoyl)-4-(4-chloromethylphenyl)cyclohexylamine from trans-N-(4-chlorobenzoyl)-4-phenylcyclohexylamine and paraformaldehyde. Melting point: 240° C., sintering from 230° C.

f) trans-N-(4-chlorobenzoyl)-N-ethyl-4-( 4-chloromethylphenyl)cyclohexylamine from trans-N-(4-chlorobenzoyl)-N-ethyl- 4-phenylcyclohexylamine and paraformaldehyde. Colourless oil. $R_f$ value: 0.38 (silica gel, petroleum ether/ethyl acetate= 3:1, v:v).

EXAMPLE H trans-4-(4-Bromomethylphenyl)-N-(4-chlorobenzoyl)-N-methylcyclohexylamine 710 mg of trans-N-(4-chlorobenzoyl)-N-methyl-4-( 4-hydroxymethylphenyl)cyclohexylamine are reacted in 20 ml of methylene chloride with 723 mg of tetrabromomethane and 572 mg of triphenylphosphine. 250 mg of the title compound are obtained, melting point 181°–183° C.

EXAMPLE I trans-N-tert. Butoxycarbonyl-N-methyl-4-( 4-methanesulphonyloxymethylphenyl)cyclohexylamine 15.4 g of trans-N-tert.butoxycarbonyl-N-methyl-4-( 4-hydroxymethylphenyl)cyclohexylamine in 120 ml of methylene chloride are mixed at 0° C. with 4.5 ml of methanesulphonic acid chloride and then 8.1 ml of triethylamine in 20 ml of methylene chloride are slowly added dropwise. After stirring overnight, water is added, the organic phase is washed with water, dried and concentrated by evaporation. After recrystallisation from diisopropylether at low temperature, 12.1 g of the title compound are obtained, melting point 138°–139° C.

EXAMPLE K trans-N-tert. Butoxycarbonyl-N-methyl-4-[4-( 3-hydroxypropyl)methylaminomethylphenyl]cyclohexylamine 6.0 g of trans-N-tert.butoxycarbonyl-N-methyl-4-( 4-methanesulphonyloxymethylphenyl)cyclohexylamine, 4.2 g of potassium carbonate and 1.6 g of N-methyl-3-hydroxypropylamine are heated together to 50° C. in 50 ml of dimethylformamide overnight. The mixture is poured into water and extracted with ethyl acetate. After drying of the organic phase, removal of the solvent and recrystallisation from petroleum ether, 7.1 g of the title compound are obtained, melting point 63°–65° C.

EXAMPLE L trans-4-[4-(3-Hydroxypropyl)methylaminomethylphenyl]-N-methylcyclohexylamine 7.1 g of trans-N-tert.butoxycarbonyl-N-methyl-4-[4-(3-hydroxypropyl)methylaminomethylphenyl]cyclohexylamine are combined with 20 ml of trifluoroacetic acid in 150 ml of methylene chloride at ambient temperature. After 2 hours, ice and 6N sodium hydroxide solution are added, the organic phase is separated off, washed, dried and evaporated down. After the residue has been recrystallised from ether, 3.1 g of the title compound are obtained, melting point 144°–146° C.

EXAMPLE M trans-N-(4-Chlorobenzoyl)-N-methyl-4-( 4-methylaminomethylphenyl)cyclohexylamine 10.3 g of trans-4-(4-tert.butoxycarbonyl-methylaminomethylphenyl)-N-( 4-chlorobenzoyl)-N-methylcyclohexylamine are reacted with trifluoroacetic acid as described in Example L. 8.12 g of the title compound are obtained, melting point 149°–151° C.

The following were prepared in the same way:

a) trans-N-(4-chlorobenzoyl)-N-cyclopropyl-4-(4-methylaminomethylphenyl)cyclohexylamine from trans-4-(4-tert.butoxycarbonyl-methylaminomethylphenyl)-N-( 4-chlorobenzoyl)-N-cyclopropylcyclohexylamine and trifluoroacetic acid. Viscous resin.

b) trans-N-allyl-N-(4-chlorobenzoyl)-4-( 4-methylaminomethylphenyl)cyclohexylamine from trans-N-allyl-N-(4-chlorobenzoyl)-4-( 4-tert.butoxycarbonyl-methylaminomethylphenyl)cyclohexylamine and trifluoroacetic acid. Colourless oil.

c) trans-N-(4-chlorobenzoyl)-N-propargyl-4-( 4-methylaminomethylphenyl)cyclohexylamine from trans-4-(4-tert.butoxycarbonyl-methylaminomethylphenyl)-N-( 4-chlorobenzoyl)-N-propargylcyclohexylamine and trifluoroacetic acid. Viscous oil.

d) trans-N-(4-chlorobenzoyl)-N-methyl-4-[4-( 1-methylaminoethyl)phenyl]cyclohexylamine from trans-4-[4-(1-tert.butoxycarbonyl-methylaminoethyl)-phenyl]-N-( 4-chlorobenzoyl)-N-methylcyclohexylamine and trifluoroacetic acid. Melting point: 153°–155° C.

e) trans-N-(4-chlorobenzoyl)-N-methyl-4-( 3-methylaminomethylphenyl)cyclohexylamine from trans-4-(3-tert.butoxycarbonyl-methylaminomethylphenyl)-N-( 4-chlorobenzoyl)-N-methylcyclohexylamine and trifluoroacetic acid. Melting point: 118°–120° C.

f) trans-N-(4-chlorobenzenesulphonyl)-N-methyl-4-( 4-methylaminomethylphenyl)cyclohexylamine from trans-(4-tert.butoxycarbonyl-methylaminomethylphenyl)-N-( 4-chlorobenzenesulphonyl)-N-methylcyclohexylamine and trifluoroacetic acid. Melting point: 105°–107° C.

g) trans-N-acetyl-N-benzyl-4-(4-methylaminomethylphenyl)-cyclohexylamine from trans-N-acetyl-N-benzyl-4-(4-tert.butoxycarbonyl-methylaminomethylphenyl)cyclohexylamine and trifluoroacetic acid. Viscous resin. $R_f$ value: 0.53 (alumina, ethyl acetate/methanol=24:1, v:v).

h) trans-N-acetyl-N-(4-fluorobenzyl)-4-( 4-methylaminomethylphenyl)cyclohexylamine from trans-N-acetyl-N-(4-fluorobenzyl)-4-( 4-tert.butoxycarbonyl-methylaminomethylphenyl)-cyclohexylamine and trifluoroacetic acid. $R_f$ value: 0.30 (alumina, methylene chloride/methanol= 40:1, v:v).

i) trans-N-(4-fluorobenzyl)-N-methanesulphonyl-4-( 4-methylaminomethylphenyl)cyclohexylamine from trans-4-(4-tert.butoxycarbonyl-methylaminomethylphenyl)-N-( 4-fluorobenzyl)-N-methanesulphonyl-cyclohexylamine and trifluoroacetic acid.

$R_f$ value: 0.38 (alumina, methylene chloride/methanol= 40:1, v:v).

j) trans-4-(4-methylaminomethylphenyl)-N-methyl-N-( 4-phenyl-3-butenoyl)cyclohexylamine from trans-4-(4-tert.butoxycarbonyl-methylaminomethylphenyl)-N-methyl-N-( 4-phenyl- 3-butenoyl)cyclohexylamine and trifluoroacetic acid. Oil.

$R_f$ value: 0.2 (alumina, petroleum ether/ethyl acetate/methanol=10:10:3, v:v:v).

k) trans-N-ethyl-N-(4-phenyl-3-butenoyl)-4-( 4-methylaminomethylphenyl)cyclohexylamine from trans-4-(4-tert.butoxycarbonyl-methylaminomethylphenyl)-N-ethyl-N-( 4-phenyl-3-butenoyl)cyclohexylamine and trifluoroacetic acid. Oil. $R_f$ value: 0.24 (alumina, petroleum ether/ethyl acetate/methanol=10:10:1, v:v:v).

l) trans-N-benzyl-N-(4-phenyl-3-butenoyl)-4-( 4-methylaminomethylphenyl)cyclohexylamine from trans-N-benzyl-N-(4-phenyl-3-butenoyl)-4-( 4-tert.butoxycarbonyl-methylaminomethylphenyl)-cyclohexylamine and trifluoroacetic acid. Oil. $R_f$ value: 0.4 (alumina, petroleum ether/ethyl acetate/methanol=10:10:1, v:v:v).

m) cis-N-(4-chlorobenzoyl)-N-methyl-4-( 4-methylaminomethylphenyl)cyclohexylamine from cis-4-(4-tert.butoxycarbonyl-methylaminomethylphenyl)-N-( 4-chlorobenzoyl)-N-methyl-cyclohexylamine and trifluoroacetic acid. Melting point: 110°–112° C.

n) trans-N-hexanoyl-N-methyl-4-(4-methylaminomethylphenyl)-cyclohexylamine from trans-4-( 4-tert.butoxycarbonyl-methylaminomethylphenyl)-N-hexanoyl-N-methylcyclohexylamine and trifluoroacetic acid. Melting point: 42°–44° C.

o) trans-N-(4-chlorobenzenesulphonyl)-N-methyl-4-[4-( 1-methylaminoethyl)phenyl]cyclohexylamine from trans-4-[4-( 1-tert.butoxycarbonyl-methylaminoethyl)phenyl]-N-( 4-chlorobenzenesulphonyl)-N-methylcyclohexylamine and trifluoroacetic acid. Melting point: 82°–85° C.

Examples of the preparation of the end products:

EXAMPLE 1 trans-N-(4-Chlorobenzoyl)-N-methyl-4-[4-( 3-hydroxypropyl)-methylaminomethylphenyl]cyclohexylamine 5.0 g (0,013 Mol) of trans-N-(4-chlorobenzoyl)-N-methyl- 4-(4-methylaminomethylphenyl)cyclohexylamine, 2.1 g (0.0148 Mol) of potassium carbonate and 2.1 g (0.015 mol) of 3-bromo-1-propanol are stirred together in 30 ml of dimethylformamide at ambient temperature for 40 hours. Then the reaction mixture is poured into water and extracted with ethyl acetate. After washing with water and saturated saline solution the mixture is evaporated down and the residue is purified by column chromatography (aluminium oxide, ethyl acetate/methanol= 70:1 to 40:1, v:v). 3.8 g (68% of theory) of the title compound are obtained, melting point 98°–100° C. $^1$H-NMR spectrum (200 MHz, CDCl$_3$); signals at ppm: 1.35 (m, 1H) , 1.6–2.1 (m, 9H) , 2.2 (2s, 3H) , 2.35–2.55 (m, 1H), 2.6 (t,2H), 2.8–3.1 (m,3H), 3.45 (s,2H), 3.75 (t,2H), 3.6+4.6 (t+m, 1H), 7.0–7.5 (m,8H).

The hydrochloride of the above compound was obtained by the addition of ethereal hydrochloric acid to a solution of the base in acetone followed by precipitation of the hydrochloride with ether. Melting point: 162°–164° C.

The following were obtained in the same way:

a) trans-4-(4-aminocarbonylmethyl-methylaminomethylphenyl)-N-( 4-chlorobenzenesulphonyl)-N-methylcyclohexylamine from trans-N-(4-chlorobenzenesulphonyl)-N-methyl-4-( 4-methylaminomethylphenyl)cyclohexylamine and chloroacetamide. Melting point: 133°–135° C.

b) trans-4-(4-aminocarbonylmethyl-methylaminomethylphenyl)-N-( 4-chlorobenzoyl)-N-methylcyclohexylamine from trans-N-(4-chlorobenzoyl)-N-methyl-4-( 4-methylaminomethylphenyl)cyclohexylamine and chloroacetamide. Melting point: 138°–140° C.

c) trans-N-(4-chlorobenzenesulphonyl)-N-methyl-4-[4-( 2-methoxyethyl)methylaminomethylphenyl]cyclohexylamine from trans-N-(4-chlorobenzenesulphonyl)-N-methyl-4-( 4-methylaminomethylphenyl)cyclohexylamine and ( 2-bromomethyl)methylether. Melting point: 55°–57° C.

d) trans-N-(4-chlorobenzoyl)-N-methyl-4-[4-( 3-cyanopropyl)-methylaminomethylphenyl]cyclohexylamine from trans-N-(4-chlorobenzoyl)-N-methyl-4-( 4-methylaminomethylphenyl)cyclohexylamine and 4-bromobutyronitrile. Melting point: 112°–114° C.

e) trans-4-[4-( 1-aminocarbonylethyl)methylaminomethyl-phenyl]-N-( 4-chlorobenzoyl)-N-methyl-cyclohexylamine from trans-N-(4-chlorobenzoyl)-N-methyl-4-( 4-methylaminomethylphenyl)cyclohexylamine and 2-chloropropionamide. Melting point: 160°–162° C.

f) cis-N-(4-chlorobenzoyl)-N-methyl-4-[4-( 3-hydroxypropyl)-methylaminomethylphenyl]cyclohexylamine from cis-N-(4-chlorobenzoyl)-N-methyl-4-( 4-methylaminomethylphenyl)cyclohexylamine and 3-hydroxypropylamine. Melting point: 62°–64° C.

g) trans-4-[4-( 3-cyanopropyl)methylaminomethylphenyl]-N-hexanoyl-N-methylcyclohexylamine from trans-N-hexanoyl-N-methyl-4-( 4-methylaminomethylphenyl)cyclohexylamine and 4-bromobutyronitrile. Colourless oil. R$_f$ value: 0.56 (alumina, ethyl acetate/petroleum ether= 1:2, v:v).

h) trans-N-hexanoyl-N-methyl-4-[4-( 2-methoxyethyl)methylaminomethylphenyl]cyclohexylamine from trans-N-hexanoyl-N-methyl-4-( 4-methylaminomethylphenyl)cyclohexylamine and (2-bromoethyl)methylether. Oil. R$_f$ value: 0.68 (alumina, ethyl acetate/petroleum ether= 1:1, v:v).

i) trans-N-(4-chlorobenzoyl)-N-methyl-4-[4-( 2-methoxyethyl)methylaminomethylphenyl)cyclohexylamine from trans-N-(4-chlorobenzoyl)-N-methyl-4-( 4-methylaminomethylphenyl)cyclohexylamine and (2-bromoethyl)methylether. Melting point: 127°–129° C.

j) trans-N-(4-chlorobenzoyl)-N-methyl-4-( 4-dimethylaminocarbonylmethyl-methylaminomethylphenyl)-cyclohexylamine from trans-N-(4-chlorobenzoyl)-N-methyl-4-( 4-methylaminomethylphenyl)cyclohexylamine and N,N-dimethylchloroacetamide. Melting point: 95°–97° C.

k) trans-N-(4-chlorobenzenesulphonyl)-N-methyl-4-[4-( 2-hydroxyethyl)methylaminomethylphenyl]cyclohexylamine from trans-N-(4-chlorobenzenesulphonyl)-N-methyl-4-( 4-methylaminomethylphenyl)cyclohexylamine and bromoethanol. Melting point: 76°–78° C.

l) trans-N-(4-chlorobenzenesulphonyl)-N-methyl-4-[4-( 3-hydroxypropyl)methylaminomethylphenyl]cyclohexylamine from trans-N-(4-chlorobenzenesulphonyl)-N-methyl-4-( 4-methylaminomethylphenyl)cyclohexylamine and 3-bromo-1-propanol. Melting point: 69°–71° C.

m) trans-N-(4-chlorobenzenesulphonyl)-N-methyl-4-[4-( 3-cyanopropyl)methylaminomethylphenyl]cyclohexylamine from trans-N-(4-chlorobenzenesulphonyl)-N-methyl-4-( 4-methylaminomethylphenyl)cyclohexylamine and 4-bromobutyronitrile. R$_f$ value: 0.29 (alumina, petroleum ether/ ethyl acetate= 3:1, v:v).

n) trans-N-(4-chlorobenzenesulphonyl)-N-methyl-4-( 4-methylaminocarbonylmethyl-methylaminomethylphenyl)-cyclohexylamine from trans-N-(4-chlorobenzenesulphonyl)-N-methyl-4-(4-methylaminomethylphenyl)cyclohexylamine and N-methylchloroacetamide. Melting point: 115°–117° C.

o) trans-N-(4-chlorobenzenesulphonyl)-N-methyl-4-[4-( 5-hydroxypentyl)methylaminomethylphenyl]cyclohexylamine from trans-N-(4-chlorobenzenesulphonyl)-N-methyl-4-( 4-methylaminomethylphenyl)cyclohexylamine and 5-chloro- 1-pentanol. Oil. R$_f$ value: 0.71 (alumina, ethyl acetate/methanol=50:1, v:v).

p) trans-4-(4-aminocarbonylmethyl-methylaminomethylphenyl)-N-hexanoyl-N-methylcyclohexylamine from trans-N-hexanoyl-N-methyl-4-( 4-methylaminomethylphenyl)-cyclohexylamine and chloroacetamide. Melting point: 84°–86° C.

q) trans-N-acetyl-N-benzyl-4-[4-( 3-hydroxypropyl)-methylaminomethylphenyl]cyclohexylamine from trans-N-acetyl-N-benzyl-4-( 4-methylaminomethylphenyl)cyclohexylamine and 3-bromo-1-propanol. Oil. R$_f$ value: 0.66 (alumina, ethyl acetate/methanol=50:1, v:v).

r) trans-N-acetyl-N-benzyl-4-(4-aminocarbonylmethylmethylaminomethylphenyl)cyclohexylamine from trans-N-acetyl-N-benzyl-4-( 4-methylaminomethylphenyl)-cyclohexylamine and chloroacetamide. Melting point: 99°–101° C.

s) trans-4-( 4-aminocarbonylmethyl-methylaminomethylphenyl)-N-( 4-fluorobenzyl)-N-methanesulphonyl-cyclohexylamine from trans-N-(4-fluorobenzyl)-N-methanesulphonyl-4-( 4-methylaminomethylphenyl)cyclohexylamine and iodoacetamide. Melting point: 114°–116° C.

t) trans-N-(4-fluorobenzyl)-N-methanesulphonyl-4-[4-( 3-hydroxypropyl)methylaminomethylphenyl]-cyclohexylamine from trans-N-(4-fluorobenzyl)-N-methanesulphonyl-4-(4-methylaminomethylphenyl)cyclohexylamine and 3-bromo-1-propanol. Melting point: 79°–81° C.

u) trans-N-(4-chlorobenzoyl)-N-cyclopropyl-4-[4-( 3-hydroxypropyl)methylaminomethylphenyl]-cyclohexylamine from trans-N-(4-chlorobenzoyl)-N-cyclopropyl-4-( 4-methylaminomethylphenyl)cyclohexylamine and 3-bromo-1-propanol. Melting point: 118°–123° C.

v) trans-N-(4-chlorobenzoyl)-N-propargyl-4-[4-( 3-hydroxypropyl)methylaminomethylphenyl]cyclohexylamine from trans-N-(4-chlorobenzoyl)-N-propargyl-4-( 4-methylaminomethylphenyl)cyclohexylamine and 3-bromo-1-propanol. Oil. $R_f$ value: 0.53 (alumina, methylene chloride/methanol=50:1, v:v).

w) trans-N-allyl-N-(4-chlorobenzoyl)-4-[4-( 3-hydroxypropyl)methylaminomethylphenyl]cyclohexylamine from trans-N-allyl-N-(4-chlorobenzoyl)-4-( 4-methylaminomethylphenyl)cyclohexylamine and 3-bromo-1-propanol. Oil. $R_f$ value: 0.56 (alumina, methylene chloride/methanol= 50:1, v:v).

x) trans-N-(4-chlorobenzoyl)-N-methyl-4-[3-( 3-hydroxypropyl)methylaminomethylphenyl]cyclohexylamine from trans-N-(4-chlorobenzoyl)-N-methyl-4-( 3-methylaminomethylphenyl)cyclohexylamine and 3-bromo-1-propanol. Wax. $R_f$ value: 0.68 (alumina, ethyl acetate).

y) trans-N-(4-chlorobenzoyl)-N-methyl-4-[4-(1-(( 3-hydroxypropyl))methylaminoethyl)phenyl]-cyclohexylamine from trans-N-(4-chlorobenzoyl)-N-methyl-4-[4-( 1-methylaminoethyl)phenyl]cyclohexylamine and 3-bromo-1-propanol. Melting point: 88°–90° C.

z) trans-N-(4-chlorobenzoyl)-N-methyl-4-[4-(1-( 2-hydroxyethyl)methylaminoethyl)phenyl]cyclohexylamine from trans-N-(4-chlorobenzoyl)-N-methyl-4-[4-( 1-methylaminoethyl)phenyl]cyclohexylamine and bromoethanol. Melting point: 118°–120° C.

aa) trans-4-[4-( 1-aminocarbonylmethyl-methylaminoethyl)-phenyl]-N-( 4-chlorobenzoyl)-N-methylcyclohexylamine from trans-N-(4-chlorobenzoyl)-N-methyl-4-[4-( 1-methylaminoethyl)phenyl]cyclohexylamine and iodoacetamide. Melting point: 173°–175° C.

ab) trans-N-(4-chlorobenzenesulphonyl)-N-methyl-4-[ 4-(1-(3-hydroxypropyl)methylaminoethyl)phenyl]-cyclohexylamine from trans-N-(4-chlorobenzenesulphonyl)-N-methyl-4-[ 4-(1-methylaminoethyl)phenyl]cyclohexylamine and 3-bromo- 1-propanol. Oil. $R_f$ value: 0.4 (alumina, petroleum ether/ethyl acetate=1:1, v:v).

ac) trans N-(4-chlorobenzenesulphonyl)-N-methyl-4-[ 4-(1-(2-hydroxyethyl)methylaminoethyl)phenyl]-cyclohexylamine from trans-N-(4-chlorobenzenesulphonyl)-N-methyl-4-[ 4-(1-methylaminoethyl)phenyl]cyclohexylamine and bromoethanol. Melting point: 80°–82° C.

ad) trans-4-[4-(1-aminocarbonylmethyl-methylaminoethyl)-phenyl]-N-( 4-chlorobenzenesulphonyl)-N-methylcyclohexylamine from trans-N-(4-chlorobenzenesulphonyl)-N-methyl-4-[ 4-(1-methylaminoethyl)phenyl]cyclohexylamine and iodoacetamide. Melting point: 170°–172° C.

ae) trans-4-[4-(2-hydroxyethyl)methylamino-methylphenyl]-N-methyl-N-(4-phenyl- 3-butenoyl)cyclohexylamine from trans-4-(4-methylaminomethylphenyl)-N-methyl-N-( 4-phenyl-3-butenoyl)cyclohexylamine and bromoethanol. Oil. $R_f$ value: 0.4 (aluminium oxide, petroleum ether/ethyl acetate/methanol=10:10:1, v:v:v).

af) trans-4-[4-(3-hydroxypropyl)methylaminomethylphenyl]-N-methyl-N-( 4-phenyl-3-butenoyl)-cyclohexylamine from trans-4-(4-methylaminomethylphenyl)-N-methyl-N-( 4-phenyl-3-butenoyl)cyclohexylamine and 3-bromo-1-propanol. Oil. $R_f$ value: 0.5 (alumina, petroleum ether/ethyl acetate/methanol=10:10:1, v:v:v).

ag) trans-4-(4-aminocarbonylmethyl-methylaminomethylphenyl)-N-methyl-N-( 4-phenyl-3-butenoyl)cyclohexylamine from trans-4-(4-methylaminomethylphenyl)-N-methyl-N-( 4-phenyl-3-butenoyl)cyclohexylamine and chloroacetamide. Melting point: 118°–120° C.

ah) trans-N-ethyl-N-(4-phenyl-3-butenoyl)-4-[4-( 3-hydroxypropyl)methylaminomethylphenyl]-cyclohexylamine from trans-N-ethyl-N-(4-phenyl-3-butenoyl)-4-( 4-methylaminomethylphenyl)cyclohexylamine and 3-bromo-1-propanol. Oil. $R_f$ value: 0.55 (alumina, petroleum ether/ethyl acetate/methanol=10:10:1, v:v:v).

ai) trans-N-benzyl-N-(4-phenyl-3-butenoyl)-4-[4-( 3-hydroxypropyl)methylaminomethylphenyl]-cyclohexylamine from trans-N-benzyl-N-(4-phenyl-3-butenoyl)-4-( 4-methylaminomethylphenyl)cyclohexylamine and 3-bromo-1-propanol. Oil. $R_f$ value: 0.45 (alumina, petroleum ether/ethyl acetate/methanol=10:10:0.5, v:v:v).

EXAMPLE 2 trans-4-[4-(3-Acetoxypropyl)methylaminomethylphenyl] -N-( 4-chlorobenzoyl)-N-methyl-cyclohexylamine 2.3 g (5.4 mMol) of trans-N-(4-chlorobenzoyl)-N-methyl-4-[4-(3-hydroxypropyl)methylaminomethylphenyl]-cyclohexylamine and 1.1 ml (6 mMol) of ethyldiisopropylamine in 50 ml of ether are mixed with 0.5 g (6 mMol) of acetylchloride, whilst cooling with ice, and the mixture is stirred for 3 hours at ambient temperature. After the reaction mixture has been diluted with ether, it is extracted with cold dilute sodium hydroxide solution, the ether phase is washed with water and saturated saline solution, dried and evaporated down. After purification by column chromatography (alumina, ethyl acetate/petroleum ether= 1:1, v:v), 1.6 g (63% of theory) of the title compound are obtained, melting point 100°–102° C. $^1$H-NMR spectrum (200 MHz, CDCl$_3$); signals at ppm: 1.35 (m,1H), 1.6–2.1 (s+m,12H), 2.2 (s,3H), 2.4–2.55 (t+m,3H), 2.8-3.1 (m,3H), 3.4 (s,2H), 3.55 and 4.6 (2m, 1H), 4.1 (t,2H), 7.0–7.45 (m,8H).

The following were obtained in the same way:

a) trans-4-[4-(3-acetoxypropyl)methylaminomethylphenyl]-N-acetyl-N-benzylcyclohexylamine from trans-N-acetyl-N-benzyl-4-[4-(3-hydroxypropyl)-methylaminomethylphenyl]cyclohexylamine and acetylchloride. Oil. $R_f$ value: 0.67 (alumina, ethyl acetate/petroleum ether= 1:1, v:v).

b) trans-4-[4-(3-ethoxycarbonyloxypropyl)methylaminomethylphenyl]-N-( 4-chlorobenzoyl)-N-methylcyclohexylamine from trans-N-(4-chlorobenzoyl)-N-methyl-4-[4-( 3-hydroxypropyl)methylaminomethylphenyl]-cyclohexylamine and ethyl chloroformate. Melting point: 87°–89° C.

c) trans-N-(4-chlorobenzoyl)-N-methyl-4-[4-( 3-pivaloyloxypropyl)methylaminomethylphenyl]-cyclohexylamine from trans-N-(4-chlorobenzoyl)-N-methyl-4-[4-( 3-hydroxypropyl)methylaminomethylphenyl]cyclohexylamine and pivaloylchloride. Melting point 100°–102° C.

d) trans-N-(4-chlorobenzoyl)-N-methyl-4-[4-( 3-isobutyryloxypropyl)methylaminomethylphenyl]-cyclohexylamine from trans-N-(4-chlorobenzoyl)-N-methyl-4-[4-( 3-hydroxypropyl)methylaminomethylphenyl]cyclohexylamine and isobutyrylchloride. Melting point: 79°–81° C.

EXAMPLE 3 trans-N-(4-Chlorobenzenesulphonyl)-N-methyl-4-[4-( 2-hydroxypropyl)methylaminomethylphenyl]cyclohexylamine 407 mg (1 mMol) of trans-N-( 4-chlorobenzenesulphonyl)-N-methyl-4-(4-methylaminomethylphenyl)cyclohexylamine and 75 mg (1.3 mMol) of 1,2-propyleneoxide are stirred in 3 ml of methanol at ambient temperature until the reaction is complete. After the solvent has evaporated off, 320 mg (69% of theory) of the title compound are obtained, melting point 90°–92° C. $^1$H-NMR spectrum (200 MHz, CDCl$_3$); signals at ppm: 1.1 (d,3H), 1.5–1.7 (m,6H), 1.8–2.0 (m,2H), 2.2 (s,3H), 2.25–2.45 (m,3H), 2.8 (s,3H), 3.35–3.7 (q,2H), 3.8–4.0 (m, 2H) , 7.1–7.8 (2q, 8H) .

The following were prepared in the same way:

a) trans-N-(4-chlorobenzoyl)-N-methyl-4-[4-(S- 2,3-dihydroxy-2-methylpropyl)methylaminomethylphenyl]-cyclohexylamine from trans-N-(4-chlorobenzoyl)-N-methyl-4-( 4-methylaminomethylphenyl)cyclohexylamine and (S)-2-methylglycidol. Melting point: 103°–105° C.

b) trans-N-(4-chlorobenzoyl)-N-methyl-4-[4-(R- 2,3-dihydroxy-2-methylpropyl)methylaminomethylphenyl]-cyclohexylamine from trans-N-(4-chlorobenzoyl)-N-methyl-4-(4-methylaminomethylphenyl)cyclohexylamine and (R)-2-methylglycidol. Melting point: 104°–106° C.

c) trans-4-[4-(S- 2,3-dihydroxypropyl)methylaminomethyl-phenyl]-N-( 4-chlorobenzoyl)-N-methylcyclohexylamine from trans-N-(4-chlorobenzoyl)-N-methyl-4-( 4-methylaminomethylphenyl)cyclohexylamine and (S)-2-glycidol. Melting point: 109°–111° C.

d) trans-4-[4-(R- 2,3-dihydroxypropyl)methylaminomethyl-phenyl]-N-( 4-chlorobenzoyl)-N-methylcyclohexylamine from trans-N-(4-chlorobenzoyl)-N-methyl-4-( 4-methylaminomethylphenyl)cyclohexylamine and (R)-2-glycidol. Melting point: 109°–111° C.

EXAMPLE 4 trans-(4-Chlorobenzenesulphonyl)-N-methyl-4-[4-( 2-oxopropyl)methylaminomethylphenyl]cyclohexylamine 285 mg (0,613 mMol) of trans-N-( 4-chlorobenzenesulphonyl)-N-methyl- 4-[4-(2-hydroxypropyl)-methylaminomethylphenyl]cyclohexylamine are oxidised using the Pfitzner-Moffatt method (380 mg (1.94 mMol) of dicyclohexylcarbodiimide, 35 mg (0.3 mMol) of trifluoroaceticacid, 0.9 ml (12.8 mMol) of dimethylsulphoxide and 2 ml of benzene). 160 mg (56% of theory) of the title compound are obtained in the form of colourless crystals, melting point 98°–100° C. $^1$H-NMR spectrum (200 MHz, CDCl$_3$); signals at ppm: 1.35 (m, 1H), 1.5–2.0 (m,9H), 2.15 (s,2H), 2.3 (s,2H), 2.4 (m, 1H) , 2.8 ( s, 3H) , 3.15 (s,2H) , 3.55 (S, 2H) , 3.9 (m, 1H) , 7.1–7.7 (2q, 8H).

EXAMPLE 5 trans-N-(4-Chlorobenzoyl)-N-methyl-4-[4-( 2-hydroxyethyl)-isopropylaminomethylphenyl]-cyclohexylamine 380 mg (1 mMol) of trans-N-(4-chlorobenzoyl)-N-methyl- 4-(4-chloromethylphenyl)cyclohexylamine are reacted with 280 mg (2 mMol) of potassium carbonate and 110 mg (1.07 mMol) of 2-isopropylaminoethanol in 3 ml of dimethylformamide as described in Example 1. 259 mg (58.5% of theory) of the title compound are obtained in the form of colourless crystals, melting point 98°–100° C.

The following were obtained in the same way:

a) trans-N-(4-chlorobenzoyl)-N-methyl-4-[4-( 2-hydroxyethyl)-n-pentylaminomethylphenyl]-cyclohexylamine from trans-N-(4-chlorobenzoyl)-N-methyl-4-( 4-chloromethylphenyl)cyclohexylamine and 2-n-pentylaminoethanol. Melting point: 40° C.

b) trans-N-(4-chlorobenzoyl)-4-[4-( 3-hydroxypropyl)-methylaminomethylphenyl]cyclohexylamine from trans-N-(4-chlorobenzoyl)-4-(4-chloromethylphenyl)-cyclohexylamine and 3-hydroxypropylmethylamine. Melting point: 157°–160° C.

c) trans-N-(4-chlorobenzoyl)-N-ethyl-4-[4-( 3-hydroxypropyl)methylaminomethylphenyl]cyclohexylamine from trans-N-(4-chlorobenzoyl)-N-ethyl-4-( 4-chloromethylphenyl)cyclohexylamine and 3-hydroxypropylmethylamine. Oil. R$_f$ value: 0.72 (alumina, ethyl acetate).

d) trans-N-(4-chlorobenzoyl)-N-cyclohexyl-4-[4-( 3-hydroxypropyl)methylaminomethylphenyl]cyclohexylamine from trans-N-(4-chlorobenzoyl)-N-cyclohexyl-4-( 4-chloromethylphenyl)cyclohexylamine and 3-hydroxypropylmethylamine. Foam. R$_f$ value: 0.41 (alumina, petroleum ether/ethyl acetate=1:1, v:v).

e) trans-N-(4-chlorobenzoyl)-N-isopropyl-4-[4-( 3-hydroxypropyl)methylaminomethylphenyl]cyclohexylamine from trans-N-(4-chlorobenzoyl)-N-isopropyl-4-( 4-chloromethylphenyl)cyclohexylamine and 3-hydroxypropylmethylamine. Oil. R$_f$ value: 0.35 (alumina, petroleum ether/ethyl acetate=1:1, v:v).

f) trans-N-(4-chlorobenzoyl)-N-neopentyl-4-[4-( 3-hydroxypropyl)methylaminomethylphenyl]cyclohexylamine from trans-N-(4-chlorobenzoyl)-N-neopentyl-4-( 4-chloromethylphenyl)cyclohexylamine and 3-hydroxypropylmethylamine. R$_f$ value: 0.58 (petroleum ether/ethyl acetate= 1:1, v:v).

g) trans-N-(4-chlorobenzoyl)-N-hexyl-4-[4-( 3-hydroxypropyl)methylaminomethylphenyl]cyclohexylamine from trans-N-(4-chlorobenzoyl)-N-hexyl-4-(4-chloromethylphenyl)cyclohexylamine and 3-hydroxypropylmethylamine. Oil. R$_f$ value: 0.53 (petroleum ether/ethyl acetate= 1:1, v:v).

EXAMPLE 6 trans-4-[4-( 3-Hydroxypropyl-methylaminomethyl)phenyl]-N-methyl-N-( 4-trifluoromethylbenzoyl)cyclohexylamine Whilst cooling with ice, a solution of 145 mg (0.69 mMol) of 4-trifluoromethylbenzoylchloride in a little methylene chloride is added dropwise to 200 mg (0.69 mMol) of trans-4-[4-( 3-hydroxypropyl)-methylaminomethylphenyl]-

N-methylcyclohexylamine and 0.1 ml (0.73 mMol) of triethylamine in 3 ml of methylene chloride and the resulting mixture is stirred for 2 hours at ambient temperature. After the reaction mixture has been diluted with ethyl acetate it is washed with water, 1N sodium hydroxide solution and saturated saline solution, then dried and evaporated down. The residue is purified by column chromatography (alumina, ethyl acetate/petroleum ether=1:1, v:v). 130 mg (40.8% of theory) of the title compound are obtained, melting point 87°–89° C.

The following were obtained in the same way:

a) trans-N-cyclopropylcarbonyl-N-methyl-4-[4-( 3-hydroxypropyl)methylaminomethylphenyl]cyclohexylamine from trans-4-[4-( 3-hydroxypropyl)methylamino-methylphenyl]-N-methylcyclohexylamine and cyclopropanecarboxylic acid chloride. Oil. $R_f$ value: 0.45 (alumina, methylene chloride/methanol= 40:1, v:v).

b) trans-N-cyclohexylcarbonyl-N-methyl-4-[4-( 3-hydroxypropyl)methylaminomethylphenyl]cyclohexylamine from trans-4-[4-( 3-hydroxypropyl)methylamino-methylphenyl]-N-methylcyclohexylamine and cyclohexanecarboxylic acid chloride. Melting point: 66°–68° C.

c) trans-4-[4-( 3-hydroxypropyl)methylaminomethylphenyl]-N-methyl-N-stearoylcyclohexylamine from trans-4-[4-( 3-hydroxypropyl)methylamino-methylphenyl]-N-methylcyclohexylamine and stearic acid chloride. Melting point: 55°–57° C.

d) trans-N-(4-fluorobenzoyl)-N-methyl-4-[4-( 3-hydroxypropyl)methylaminomethylphenyl]cyclohexylamine from trans-4-[4-( 3-hydroxypropyl)methylamino-methylphenyl]-N-methylcyclohexylamine and 4-fluorobenzoylchloride. Melting point: 105°–107° C.

e) trans-N-(4-chloro-3-methylbenzoyl)-N-methyl-4-[4-( 3-hydroxypropyl)methylaminomethylphenyl]cyclohexylamine from trans-4-[4-( 3-hydroxypropyl)methylaminomethylphenyl]-N-methylcyclohexylamine and 4-chloro-3-methylbenzoylchloride. Melting point: 98°–100° C.

f) trans-4-[4-( 3-hydroxypropyl)methylaminomethylphenyl]-N-methyl-N-( 2-naphthylacetyl)cyclohexylamine from trans-4-[4-( 3-hydroxypropyl)methylamino-methylphenyl]-N-methylcyclohexylamine and 2-naphthalene acetic acid chloride. Melting point: 127°–129° C.

g) trans-4-[4-( 3-hydroxypropyl)methylaminomethylphenyl]-N-methyl-N-( 1,2,3,4-tetrahydronaphthalene-2-carbonyl)-cyclohexylamine from trans-4-[4-( 3-hydroxypropyl)methylaminomethylphenyl]-N-methylcyclohexylamine and 1,2,3,4-tetrahydronaphthalene-2-carboxylic acid chloride. Melting point: 93°–95° C.

h) trans-4-[4-( 3-hydroxypropyl)methylaminomethylphenyl]-N-methyl-N-( 5-methylthienyl-2-carbonyl)cyclohexylamine from trans-4-[4-( 3-hydroxypropyl)methylaminomethylphenyl]-N-methylcyclohexylamine and 5-methylthiophene-2-carboxylic acid chloride. Melting point: 85°–87° C.

i) trans-N-(5-chlorothienyl-2-carbonyl)-N-methyl-4-[ 4-(3-hydroxypropyl)methylaminomethylphenyl]-cyclohexylamine from trans-4-[4-( 3-hydroxypropyl)methylaminomethylphenyl]-N-methylcyclohexylamine and 5-chlorothiophene-2-carboxylic acid chloride. Melting point: 92°–94° C.

EXAMPLE 7 trans-N-(3,4-Dichlorophenylacetyl)-N-methyl-4-[4-( 3-hydroxypropyl)methylaminomethylphenyl]cyclohexylamine 141 mg (0.68 mMol) of 3,4-dichlorophenylacetic acid in 5 ml of xylene are mixed with 112 mg (0.54 mMol) of N,N'-dicyclohexylcarbodiimide and heated to 50° C. for 1 hour. After the addition of 200 mg (0.68 mMol) of trans-4-[4-(3-hydroxypropyl)methylaminomethylphenyl]-N-methylcyclohexylamine the mixture is stirred overnight at 140° C. After cooling to ambient temperature and adding ethyl acetate, the mixture is washed with water and saturated saline solution, then dried and evaporated down. After purification by column chromatography (alumina, ethyl acetate/methanol=100:1 to 10:1, v:v), 110 mg (34% of theory) of the title compound are obtained, melting point 82°–84° C.

The following was obtained in the same way:

a) trans-4-[4-( 3-hydroxypropyl)methylaminomethylphenyl]-N-methyl-N-( 4-pentynoyl)cyclohexylamine from trans-4-[4-( 3-hydroxypropyl)methylaminomethylphenyl)-N-methylcyclohexylamine, N,N'-carbonyldiimidazole and 4-pentynoic acid. Oil. $R_f$ value: 0.66 (alumina/ethyl acetate/methanol=100:1, v:v).

In the following, the preparation of pharmaceutical administration forms is described by some examples:

EXAMPLE I

Tablets containing 5 mg of trans-N-( 4-chlorobenzoyl)-N-methyl-4-[4-( 3-hydroxypropyl)methylaminomethylphenyl]-cyclohexylamine

| Composition: 1 Tablet contains: | |
|---|---|
| Active compound | 5.0 mg |
| Lactose | 148.0 mg |
| Potato starch | 65.0 mg |
| Magnesium stearate | 2.0 mg |
| | 220.0 mg |

Preparation Process

A 10% strength mucilage is prepared from potato starch by heating. The active substance, lactose and the residual potato starch are mixed and granulated with the above mucilage through a sieve of mesh width 1.5 mm. The granules are dried at 45° C., again rubbed through the above mentioned sieve, mixed with magnesium stearate and pressed into tablets. Tablet weight: 220 mg Die: 9 mm

EXAMPLE II

Coated tablets containing 5 mg of trans-N-( 4-chlorobenzoyl)-N-methyl- 4-[4-(3-hydroxypropyl)methylaminomethylphenyl]cyclohexylamine The tablets prepared according to Example I are coated with a covering which essentially consists of sugar and talc according to a known process. The finished coated tablets are polished with the aid of beeswax. Coated tablet weight: 300 mg

EXAMPLE III

Suppositories containing 5 mg of trans-N-(4-chlorobenzoyl)-N-methyl-4-[4-(3-hydroxypropyl)methylaminomethylphenyl]cyclohexylamine

| Composition: 1 Suppository contains: | |
|---|---|
| Active compound | 5.0 mg |
| Suppository material (e.g. Witepsol W 45 ®) | 1695.0 mg |
| | 1700.0 mg |

Preparation Process

The finely powdered active substance is suspended in the molten suppository material, which has been cooled to 40° C. The material is poured out at 37° C. into slightly precooled suppository moulds. Suppository weight: 1.7 g.

EXAMPLE IV

Capsules containing 5 mg of trans-N-(4-chlorobenzoyl)-N-methyl-4-[4-(3-hydroxypropyl)methylaminomethylphenyl]-cyclohexylamine

| Composition: 1 Capsule contains: | |
|---|---|
| Active substance | 5.0 mg |
| Lactose | 82.0 mg |
| Starch | 82.0 mg |
| Magnesium stearate | 1.0 mg |
| | 170.0 mg |

Preparation Process

The powder mixture is thoroughly mixed and filled into hard gelatine capsules of size 3 on a capsule filling machine, the final weight being continuously checked.

EXAMPLE V

Tablets containing 5 mg of trans-4-[4-(3-hydroxypropyl)methylaminomethylphenyl]-N-methyl-N-(4-trifluoromethylbenzoyl)cyclohexylamine

| Composition: 1 Tablet contains: | |
|---|---|
| Active compound | 5.0 mg |
| Lactose | 148.0 mg |
| Potato starch | 65.0 mg |
| Magnesium stearate | 2.0 mg |
| | 220.0 mg |

Preparation Process

A 10% strength mucilage is prepared from potato starch by heating. The active substance, lactose and the residual potato starch are mixed and granulated with the above mucilage through a sieve of mesh width 1.5 mm. The granules are dried at 45° C., again rubbed through the above sieve, mixed with magnesium stearate and pressed into tablets. Tablet weight: 220 mg Die: 9 mm

EXAMPLE VI

Cream for topical application containing 1 g of trans-N-(4-chlorobenzoyl)-N-methyl-4-[4-(3-hydroxypropyl)methyl-aminomethylphenyl]-cyclohexylamine A formulation for topical application of the compounds of the formula I may have the following composition

| | |
|---|---|
| 1. Active compound | 1.0 g |
| 2. Stearyl alcohol | 4.0 g |
| 3. Cetyl alcohol | 4.0 g |
| 4. Mineral oil | 3.0 g |
| 5. Polysorbate 60 | 4.5 g |
| 6. Sorbitan stearate | 4.5 g |
| 7. Propylene glycol | 10.0 g |
| 8. Methylparaben | 0.18 g |
| 9. Propylparaben | 0.02 g |
| 10. Water | q.s. to 100.00 g |

Constituents 2–6 are heated to 80° C. until everything has melted. Constituent 1 is then dissolved in the oily phase. Constituents 7 and 10 are heated to 90° C. and constituents 8 and 9 are dissolved in the aqueous phase thus obtained. The aqueous phase is then added to the oil phase and stirred rapidly so that an emulsion is obtained. The mixture is then allowed to cool slowly to 50° C. in order to solidify the emulsion. The preparation is cooled to ambient temperature with further stirring.

The following example describes the preparation of a foodstuff for laying hens:

EXAMPLE VII

Foodstuff for laying hens, containing as active compound trans-N-(4-chlorobenzoyl)-N-methyl-4-[4-(3-hydroxypropyl)methylaminomethylphenyl]cyclohexylamine

| | |
|---|---|
| Maize | 633 g/kg |
| Soya bean flour | 260 g/kg |
| Meat meal | 40 g/kg |
| Feed fat | 25 g/kg |
| Soya oil | 17 g/kg |
| Bicalcium phosphate | 12 g/kg |
| Calcium carbonate | 6 g/kg |
| Vitamin/mineral mixture | 5 g/kg |
| Active compound | 2 g/kg |

After careful mixing of these components in the amounts indicated 1 kg of feed is obtained.

What is claimed is:

1. A method of inhibiting cholesterol biosynthesis in a warm-blooded animal which comprises administering to said animal an effective amount of a N,N-disubstituted arylcycloalkylamine of formula

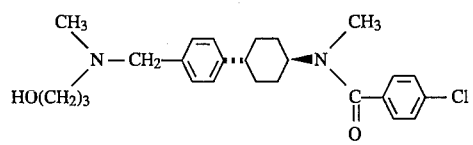

or an enantiomer, diastereomer or physiologically acceptable salt thereof.

2. A method of inhibiting cholesterol biosynthesis in a warm-blooded animal which comprises administering to said animal an effective amount of an N,N-disubstituted arylcycloalkylamine of formula I

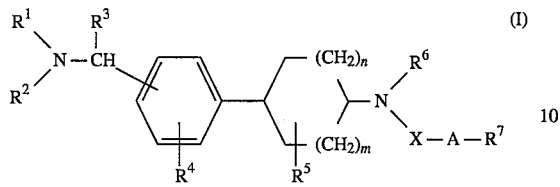

wherein n is the integer 1 or 2;

m is the integer 0 or 1;

A is a single bond, a straight-chained or branched $C_{1-17}$-alkylene group, a $C_{2-17}$ alkenylene group or a $C_{2-4}$-alkynylene group;

X is a carbonyl or sulphonyl group;

$R^1$ is a straight-chained or branched $C_{1-5}$-alkyl group;

$R^2$ is a straight-chained or branched $C_{1-5}$-alkyl group which may be substituted by one or two hydroxy groups, by an alkoxy or by an alkylcarbonyloxy group having 1 to 5 carbon atoms in the alkyl moiety, the alkyl moiety being straight-chained or branched, by an alkoxycarbonyloxy group, whilst the above-mentioned substituents may not be bound in position 1 of the alkyl group and two of these groups may not be bound to the same carbon atom, or by an aminocarbonyl, alkylaminocarbonyl, dialkylaminocarbonyl, cyano or alkylcarbonyl group;

$R^3$, $R^4$ and $R^5$, which may be identical or different, each are a hydrogen atom or an alkyl group;

$R^6$ is a hydrogen atom, a straight-chained or branched $C_{1-6}$-alkyl group, a $C_{3-6}$-cycloalkyl group, an allyl or propargyl group or an optionally halogen-substituted benzyl group;

$R^7$ is a hydrogen atom, a $C_{3-6}$-cycloalkyl group, a phenyl group optionally substituted by an alkyl group, by one or two halogen atoms or by a trifluoromethyl group, or $R^7$ is a naphthyl or tetrahydronaphthyl group or a thienyl group optionally substituted by a halogen atom or by an alkyl group;

whilst A cannot be a single bond if X is a sulphonyl group and $R^7$ is a hydrogen atom, and unless otherwise specified the above-mentioned alkyl and alkoxy moieties may each contain 1 to 3 carbon atoms and the above-mentioned halogen atoms may each be a fluorine, chlorine or bromine atom, or an enantiomer, diastereomer or physiologically acceptable salt thereof.

* * * * *